US010144735B2

(12) United States Patent
Stoermer et al.

(10) Patent No.: US 10,144,735 B2
(45) Date of Patent: Dec. 4, 2018

(54) IMMUNE RESPONSE MODIFIER COMPOSITIONS AND METHODS

(71) Applicant: 3M INNOVATIVE PROPERTIES COMPANY, St. Paul, MN (US)

(72) Inventors: Doris Stoermer, Newbury Park, CA (US); George W. Griesgraber, Eagan, MN (US); Tushar A. Kshirsagar, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 16/016,933

(22) Filed: Jun. 25, 2018

(65) Prior Publication Data

US 2018/0305357 A1 Oct. 25, 2018

Related U.S. Application Data

(62) Division of application No. 12/519,463, filed as application No. PCT/US2007/088277 on Dec. 20, 2007, now Pat. No. 10,005,772.

(60) Provisional application No. 60/871,535, filed on Dec. 22, 2006.

(51) Int. Cl.

| | |
|---|---|
| ***A61K 39/395*** | (2006.01) |
| ***C07D 471/04*** | (2006.01) |
| ***A61K 47/66*** | (2017.01) |
| ***A61K 47/68*** | (2017.01) |

(52) U.S. Cl.

CPC ............ *C07D 471/04* (2013.01); *A61K 47/66* (2017.08); *A61K 47/68* (2017.08); *A61K 47/6801* (2017.08)

(58) Field of Classification Search

None

See application file for complete search history.

(56) References Cited

U.S. PATENT DOCUMENTS

| | | | |
|---|---|---|---|
| 3,314,941 | A | 4/1967 | Littell et al. |
| 4,689,338 | A | 8/1987 | Gerster |
| 4,698,348 | A | 10/1987 | Gerster |
| 4,929,624 | A | 5/1990 | Gerster et al. |
| 4,988,815 | A | 1/1991 | Andre et al. |
| 5,037,986 | A | 8/1991 | Gerster |
| 5,175,296 | A | 12/1992 | Gerster |
| 5,238,944 | A | 8/1993 | Wick et al. |
| 5,266,575 | A | 11/1993 | Gerster |
| 5,268,376 | A | 12/1993 | Gerster |
| 5,346,905 | A | 9/1994 | Gerster |
| 5,352,784 | A | 10/1994 | Nikolaides et al. |
| 5,367,076 | A | 11/1994 | Gerster |
| 5,389,640 | A | 2/1995 | Gerster et al. |
| 5,395,937 | A | 3/1995 | Nikolaides et al. |
| 5,446,153 | A | 8/1995 | Llindstrom et al. |
| 5,482,936 | A | 1/1996 | Lindstrom |
| 5,693,811 | A | 12/1997 | Lindstrom |
| 5,741,908 | A | 4/1998 | Gerster et al. |
| 5,756,747 | A | 5/1998 | Gerster et al. |
| 5,939,090 | A | 8/1999 | Beaurline et al. |
| 6,028,076 | A | 2/2000 | Hirota et al. |
| 6,039,969 | A | 3/2000 | Tomai et al. |
| 6,069,149 | A | 5/2000 | Nanba et al. |
| 6,083,505 | A | 7/2000 | Miller et al. |
| 6,110,929 | A | 8/2000 | Gerster et al. |
| 6,113,918 | A | 9/2000 | Johnson et al. |
| 6,194,388 | B1 | 2/2001 | Krieg et al. |
| 6,194,425 | B1 | 2/2001 | Gerster et al. |
| 6,200,592 | B1 | 3/2001 | Tomai et al. |
| 6,207,646 | B1 | 3/2001 | Krieg et al. |
| 6,239,116 | B1 | 5/2001 | Krieg et al. |
| 6,245,776 | B1 | 6/2001 | Skwierczynski et al. |
| 6,303,347 | B1 | 10/2001 | Johnson et al. |
| 6,329,381 | B1 | 10/2001 | Kurimoto et al. |
| 6,331,539 | B1 | 12/2001 | Crooks et al. |
| 6,339,068 | B1 | 1/2002 | Krieg et al. |
| 6,376,501 | B1 | 4/2002 | Isobe et al. |
| 6,376,669 | B1 | 4/2002 | Rice et al. |
| 6,387,938 | B1 | 5/2002 | Mizuguchi et al. |
| 6,406,705 | B1 | 6/2002 | Davis et al. |
| 6,426,334 | B1 | 7/2002 | Agrawal et al. |
| 6,451,810 | B1 | 9/2002 | Coleman et al. |
| 6,476,000 | B1 | 11/2002 | Agrawal |
| 6,518,265 | B1 | 2/2003 | Kato et al. |
| 6,525,028 | B1 | 2/2003 | Johnson et al. |
| 6,525,064 | B1 | 2/2003 | Dellaria et al. |
| 6,541,485 | B1 | 4/2003 | Crooks et al. |
| 6,545,016 | B1 | 4/2003 | Dellaria et al. |

(Continued)

FOREIGN PATENT DOCUMENTS

| | | |
|---|---|---|
| EP | 0 394 026 | 10/1990 |
| EP | 1 104 764 | 6/2001 |
| JP | 9-208584 | 8/1997 |
| JP | 11-080156 A | 3/1999 |
| JP | 11-222432 | 8/1999 |
| JP | 2000-247884 | 9/2000 |
| WO | WO 00/40228 | 7/2000 |
| WO | WO 00/47719 | 8/2000 |
| WO | WO 02/08905 | 1/2002 |
| WO | WO 02/36592 | 5/2002 |
| WO | WO 2003/094836 | 11/2003 |
| WO | WO 2004/101957 | 11/2004 |
| WO | WO 05/018551 | 3/2005 |
| WO | WO 05/018555 | 3/2005 |

(Continued)

OTHER PUBLICATIONS

Wozniak et al., "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

(Continued)

*Primary Examiner* — Patricia Duffy
(74) *Attorney, Agent, or Firm* — Eric E. Silverman

(57) ABSTRACT

The present invention provides an immune response modifier (IRM) composition that includes an IRM moiety and a second active moiety covalently linked to the IRM moiety, wherein the covalent link comprises a labile bond directly attached to the IRM moiety.

13 Claims, 5 Drawing Sheets

(56) References Cited

U.S. PATENT DOCUMENTS

| | | | |
|---|---|---|---|
| 6,545,017 | B1 | 4/2003 | Dellaria et al. |
| 6,558,951 | B1 | 5/2003 | Tomai et al. |
| 6,573,273 | B1 | 6/2003 | Crooks et al. |
| 6,649,172 | B2 | 11/2003 | Johnson |
| 6,656,469 | B1 | 12/2003 | Svensson et al. |
| 6,656,938 | B2 | 12/2003 | Crooks et al. |
| 6,660,735 | B2 | 12/2003 | Crooks et al. |
| 6,660,747 | B2 | 12/2003 | Crooks et al. |
| 6,664,260 | B2 | 12/2003 | Charles et al. |
| 6,664,264 | B2 | 12/2003 | Dellaria et al. |
| 6,664,265 | B2 | 12/2003 | Crooks et al. |
| 6,667,312 | B2 | 12/2003 | Bonk et al. |
| 6,670,372 | B2 | 12/2003 | Charles et al. |
| 6,677,347 | B2 | 1/2004 | Crooks et al. |
| 6,677,348 | B2 | 1/2004 | Heppner et al. |
| 6,677,349 | B1 | 1/2004 | Griesgraber |
| 6,683,088 | B2 | 1/2004 | Crooks et al. |
| 6,696,465 | B2 | 2/2004 | Dellaria et al. |
| 6,706,728 | B2 | 3/2004 | Hedenstrom et al. |
| 6,743,920 | B2 | 6/2004 | Lindstrom et al. |
| 6,756,382 | B2 | 6/2004 | Coleman et al. |
| 6,797,718 | B2 | 9/2004 | Dellaria et al. |
| 6,818,650 | B2 | 11/2004 | Griesgraber |
| 6,841,678 | B2 | 1/2005 | Merli et al. |
| 6,852,861 | B2 | 2/2005 | Merli et al. |
| 7,091,214 | B2 | 8/2006 | Hays et al. |
| 7,163,947 | B2 | 1/2007 | Griesgraber et al. |
| 7,387,271 | B2 | 6/2008 | Noelle et al. |
| 7,427,629 | B2 | 9/2008 | Kedl et al. |
| 7,485,432 | B2 | 2/2009 | Fink et al. |
| 8,188,111 | B2 | 5/2012 | Kshirsagar et al. |
| 2002/0016332 | A1 | 2/2002 | Slade |
| 2002/0055517 | A1 | 5/2002 | Smith |
| 2002/0058674 | A1 | 5/2002 | Hedenstrom et al. |
| 2002/0107262 | A1 | 8/2002 | Lindstrom |
| 2002/0110840 | A1 | 8/2002 | Tomai et al. |
| 2003/0096835 | A1 | 5/2003 | Crooks et al. |
| 2003/0130299 | A1 | 7/2003 | Crooks et al. |
| 2003/0133913 | A1 | 7/2003 | Tomai et al. |
| 2003/0139364 | A1 | 7/2003 | Krieg et al. |
| 2003/0144286 | A1 | 7/2003 | Frenkel et al. |
| 2003/0161797 | A1 | 8/2003 | Miller et al. |
| 2003/0185835 | A1 | 10/2003 | Braun |
| 2003/0199461 | A1 | 10/2003 | Averett et al. |
| 2003/0199538 | A1 | 10/2003 | Skwierczynski et al. |
| 2004/0013728 | A1 | 1/2004 | Oh et al. |
| 2004/0014779 | A1 | 1/2004 | Gorden et al. |
| 2004/0091491 | A1 | 5/2004 | Kedl et al. |
| 2004/0132079 | A1 | 7/2004 | Gupta et al. |
| 2004/0141950 | A1 | 7/2004 | Noelle et al. |
| 2004/0147543 | A1 | 7/2004 | Hays et al. |
| 2004/0162309 | A1 | 8/2004 | Gorden et al. |
| 2004/0171086 | A1 | 9/2004 | Fink et al. |
| 2004/0175336 | A1 | 9/2004 | Egging et al. |
| 2004/0176367 | A1 | 9/2004 | Griesgraber et al. |
| 2004/0180919 | A1 | 9/2004 | Lee et al. |
| 2004/0181130 | A1 | 9/2004 | Fox et al. |
| 2004/0181211 | A1 | 9/2004 | Elliott et al. |
| 2004/0191833 | A1 | 9/2004 | Fink et al. |
| 2004/0192585 | A1 | 9/2004 | Fox et al. |
| 2004/0197865 | A1 | 10/2004 | Gupta et al. |
| 2004/0202720 | A1 | 10/2004 | Wightman et al. |
| 2004/0214851 | A1 | 10/2004 | Birmachu et al. |
| 2004/0265351 | A1 | 12/2004 | Miller et al. |
| 2005/0048072 | A1 | 3/2005 | Kedl et al. |
| 2005/0054590 | A1 | 3/2005 | Averett |
| 2005/0085500 | A1 | 4/2005 | Gutman et al. |
| 2005/0107322 | A1 | 5/2005 | O'Hagan et al. |
| 2005/0136065 | A1 | 6/2005 | Valiante, Jr. |
| 2005/0165236 | A1 | 7/2005 | Colombo et al. |
| 2005/0245562 | A1 | 11/2005 | Garcia-Echeverria et al. |
| 2006/0045885 | A1 | 3/2006 | Kedl et al. |
| 2006/0100229 | A1 | 5/2006 | Hays et al. |
| 2006/0142202 | A1 | 6/2006 | Alkan et al. |
| 2006/0210588 | A1 | 9/2006 | Bachmann et al. |
| 2008/0193468 | A1 | 8/2008 | Levy et al. |
| 2009/0028874 | A1 | 1/2009 | Van Der Burg et al. |

FOREIGN PATENT DOCUMENTS

| | | |
|---|---|---|
| WO | WO 05/018556 | 3/2005 |
| WO | WO 05/020999 | 3/2005 |
| WO | WO 05/032484 | 4/2005 |
| WO | WO 05/048933 | 6/2005 |
| WO | WO 05/048945 | 6/2005 |
| WO | WO 05/051317 | 6/2005 |
| WO | WO 05/051324 | 6/2005 |
| WO | WO 05/054237 | 6/2005 |
| WO | WO 05/054238 | 6/2005 |
| WO | WO 05/066169 | 7/2005 |
| WO | WO 05/066170 | 7/2005 |
| WO | WO 05/066172 | 7/2005 |
| WO | WO 05/076783 | 8/2005 |
| WO | WO 05/079195 | 9/2005 |
| WO | WO 2005/082023 | 9/2005 |
| WO | WO 05/094531 | 10/2005 |
| WO | WO 2005/110013 | 11/2005 |
| WO | WO 05/123079 | 12/2005 |
| WO | WO 05/123080 | 12/2005 |
| WO | WO 06/009826 | 1/2006 |
| WO | WO 06/009832 | 1/2006 |
| WO | WO 06/026760 | 3/2006 |
| WO | WO 06/028451 | 3/2006 |
| WO | WO 06/028545 | 3/2006 |
| WO | WO 06/028962 | 3/2006 |
| WO | WO 06/029115 | 3/2006 |
| WO | WO 06/031878 | 3/2006 |
| WO | WO 06/038923 | 4/2006 |
| WO | WO 06/065280 | 6/2006 |
| WO | WO 06/074003 | 7/2006 |
| WO | WO 06/074046 | 7/2006 |
| WO | WO 06/004737 | 8/2006 |
| WO | WO 06/083400 | 8/2006 |
| WO | WO 06/083440 | 8/2006 |
| WO | WO 06/086449 | 8/2006 |
| WO | WO 06/086633 | 8/2006 |
| WO | WO 06/091394 | 8/2006 |
| WO | WO 06/091567 | 8/2006 |
| WO | WO 06/091568 | 8/2006 |
| WO | WO 06/091647 | 8/2006 |
| WO | WO 2006/086634 | 8/2006 |
| WO | WO 06/098852 | 9/2006 |
| WO | WO 2006/093514 | 9/2006 |
| WO | WO 06/107771 | 10/2006 |
| WO | WO 06/107851 | 10/2006 |
| WO | WO 06/107853 | 10/2006 |
| WO | WO 2006/107753 | 10/2006 |
| WO | WO 06/121528 | 11/2006 |
| WO | WO 07/028129 | 3/2007 |
| WO | WO 07/030775 | 3/2007 |
| WO | WO 07/030777 | 3/2007 |
| WO | WO 07/035935 | 3/2007 |
| WO | WO 07/056112 | 5/2007 |

OTHER PUBLICATIONS

Brennan et al., "Automated Bioassay of Interferons in Micro-test Plates.", *Biotechniques*, Jun./Jul., 78, 1983.

Testerman et al., "Cytokine Induction by the Immunomodulators Imiquimod and S-27609.", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem.* 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

Baranov et al., "Pyrazoles, Imidazoles, and Other 5-Membered Rings.", (1976). *Chem. Abs.* 85, 94362, (1976).

Berényi et al., "Ring Transformation of Condensed Dihydro-as-triazines.", *J. Heterocyclic Chem.*, 18, pp. 1537-1540 (1981).

(56) References Cited

OTHER PUBLICATIONS

Chollet et al., "Development of a Topically Active Imiquimod Formulation.", *Pharmaceutical Development and Technology*, 4(1), pp. 35-43 (1999).

Izumi et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines.", *Bioorganic & Medicinal Chemistry*, 11, pp. 2541-2550 (2003).

Heil et al., Science, "Species-Specific Recognition of Single-Stranded RNA via Toll-Like Receptor 7 and 8," vol. 303, pp. 1526-1529, Mar. 5, 2004.

Toki, B.E. et al., J. Org. Chem, "Protease-Mediated Fragmentation of p-Amidobenzyl Ethers: A New Strategy for the Activation of Anticancer Prodrugs," 2002, 67, 1866-1872.

Jeffrey, S.C., et al., J. Med. Chem. "Design, Synthesis, and in Vitro Evaluation of Dipeptide-Based Antibody Minor Groove Binder Conjugates," 2005, 48, 1344-1358.

Sun, M.M.C. et al., Bioconjugate Chem. "Reduction-Alkylation Strategies for the Modification of Specific Monoclonal Antibody Disulfides," 2005, 16, 1282-1290.

Hermanson, G., "Bioconjugate Techniques," 1996, Academic Press, Chapter 5, "Heterobifunctional Cross-Linkers," pp. 228-285.

W. Greene and P.G. M. Wuts, Protective Groups in Organic Synthesis, John Wiley & Sons, New York, USA, 1991.

Harandi, et al., Current Opinion in Investigational Drugs, "Recent Developments in Mucosal Immunomodulatory Adjuvants," 2003, vol. 4, No. 2, pp. 156-161.

Lynch, Infection and Immunity, "Increased Protection Against Pneumococcal Disease by Mucolsal Administration of Conjugate Vaccine Plus Interleukin-12," vol. 71, No. 8, Aug. 2003, pp. 4780-4788.

Couch, M.D., N Engl J Med 350:9, "Nsal Vaccination, *Escherichia coli* Enterotoxin, and Bell's Palsy," Feb. 26, 2004, pp. 860-861.

Singh, et al., Nature Biotechology, "Advances in Vaccine Adjuvants," vol. 17, Nov. 1999, pp. 1075-1081.

Lubben, et al., Advanced Drug Delivery Reviews, "Chitosan for Mucosal vaccination," 52 (2001), pp. 239-144.

Van Ginkel, et al., Emerging Infectious Diseases, "Vaccines for Mucosal Immunity to Combat Emerging Infectious Diseases," vol. 6, No. 2, Mar.-Apr. 2000, pp. 123-132.

Belyakov, et al., Proc. Natl. Acad. Sci. USA, "Mucosal Vaccination Overcomes the Barrier to Recombinant Vaccinia Immunization Caused by Preexisting Poxvirus Immunity," vol. 96, Apr. 1999, pp. 4512-4517.

Von Hoegen, Advanced Drug Delivery Reviews, "Synthetic Biomimetic Supra Molecular Biovector™ (SMBV™) Particles for Nasal Vaccine Delivery," 51 2001, pp. 113-125.

Gupta, et al., Vaccine, Adjuvants for Human Vaccines—Current Status, Problems and Future Prospects, vol. 13, No. 14, 1995, pp. 1263-1276.

Suenobu, Vaccine, Nasal Vaccination Inducaes the Ability to Eliminate Candida Colonization Without Influencing the Pre-Existing Antigen-Specific IgE Abs: a Possibility for the Control of Candida-Related Atopic Dermatitis.

Hamajima et al. A Macromolecular Multicomponent Peptide Vaccine Prepared Using the Glutaraldehyde Conjugation Method with Strong Immunogicity for HIV-1. Clinical Immunology and Immunopathology, Dec. 1995, vol. 77, No. 3, p. 374-379.

IMMUNE RESPONSE MODIFIER COMPOSITIONS AND METHODS

CROSS REFERENCE TO RELATED APPLICATIONS

This application is a divisional of U.S. patent application Ser. No. 12/519,463, filed Jan. 27, 2010, now U.S. patent Ser. No. 10/005,772 which is a national stage filing under 35 U.S.C. 371 of PCT/US2007/088277, filed Dec. 20, 2007, which claims the benefit of U.S. Provisional Application No. 60/871,535 filed Dec. 22, 2006, the disclosure of which is incorporated by reference in their entirety herein.

BACKGROUND

There has been a major effort in recent years, with significant success, to discover new drug compounds that act by stimulating certain key aspects of the immune system, as well as by suppressing certain other aspects (see, e.g., U.S. Pat. Nos. 6,039,969 and 6,200,592). These compounds, referred to herein as immune response modifiers (IRMs), appear to act through basic immune system mechanisms known as Toll-like receptors (TLRs) to induce selected cytokine biosynthesis, induction of co-stimulatory molecules, and increased antigen-presenting capacity.

They may be useful for treating a wide variety of diseases and conditions. For example, certain IRMs may be useful for treating viral diseases (e.g., human papilloma virus, hepatitis, herpes), neoplasias (e.g., basal cell carcinoma, squamous cell carcinoma, actinic keratosis, melanoma), and $T_H2$-mediated diseases (e.g., asthma, allergic rhinitis, atopic dermatitis), autoimmune diseases (e.g., multiple sclerosis), and are also useful as vaccine adjuvants.

Many of the IRM compounds are small organic molecule imidazoquinoline amine derivatives (see, e.g., U.S. Pat. No. 4,689,338), but a number of other compound classes are known as well (see, e.g., U.S. Pat. Nos. 5,446,153; 6,194,425; and 6,110,929; and International Publication Number WO 2005/079195) and more are still being discovered. Other IRMs have higher molecular weights, such as oligonucleotides, including CpGs (see, e.g., U.S. Pat. No. 6,194,388).

In view of the great therapeutic potential for IRMs, and despite the important work that has already been done, there is a substantial ongoing need to expand their uses and therapeutic benefits.

SUMMARY

The present invention exploits the observation that the activity of certain IRM compounds can be significantly decreased, even eliminated, by making a covalent chemical substitution at certain specified sites of the compound.

Accordingly, the present invention provides an immune response modifier (IRM) conjugate that includes an IRM moiety and a second active moiety covalently linked to the IRM moiety, wherein the covalent link comprises a labile bond directly attached to the IRM moiety.

In another aspect, the present invention also provides method of generating an immune response. Generally, the method includes administering an IRM conjugate that includes an IRM moiety and a second active moiety covalently linked to the IRM moiety, wherein the covalent link includes a labile bond directly attached to the IRM moiety, to a cell population capable of generating an IRM-induced immune response; allowing the labile bond to be cleaved, thereby generating a free IRM compound; and allowing the free IRM compound to contact cells of the cell population, thereby generating an IRM-induced immune response.

In another aspect, the present invention also provides a functionalized IRM of the Formula III described below.

Various other features and advantages of the present invention should become readily apparent with reference to the following detailed description, examples, claims and appended drawings. In several places throughout the specification, guidance is provided through lists of examples. In each instance, the recited list serves only as a representative group and should not be interpreted as an exclusive list.

DETAILED DESCRIPTION OF ILLUSTRATIVE EMBODIMENTS OF THE INVENTION

Figure 1:
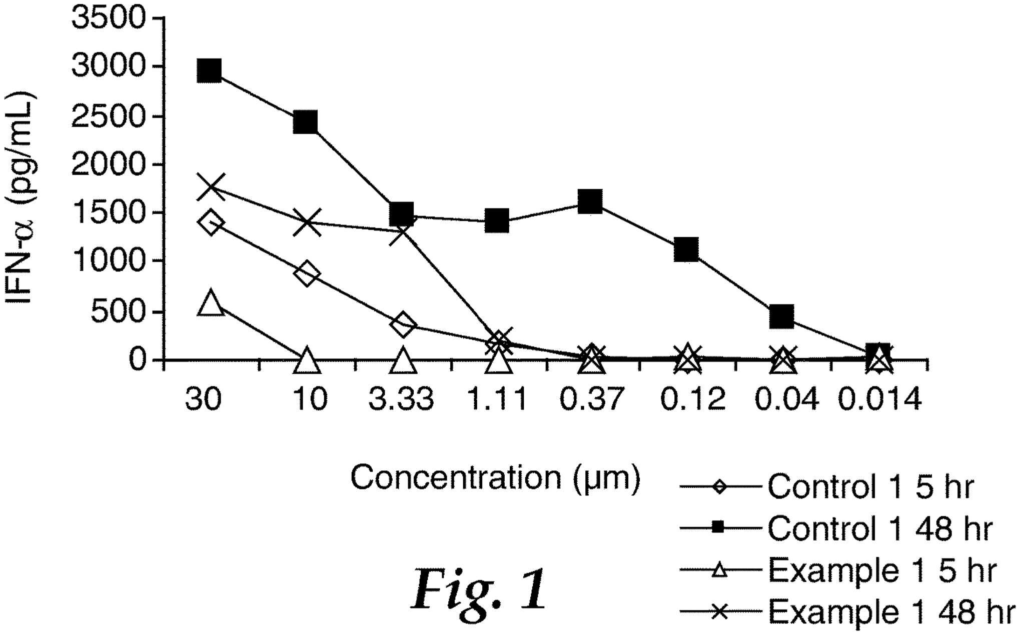
FIG. 1 is a line graph comparing IFN-α induction by an IRM conjugate composition of the invention compared to its parent IRM compound.

It has been found that making a chemical substitution at certain specified sites on certain IRM compounds can significantly decrease, even eliminate, the immunomodulatory activity of the parent IRM compound. This observation can be exploited by using conjugates in which an IRM moiety is covalently attached via a labile bond at one of the sites that reduces the activity of the IRM moiety. In this way, a relatively inactive form of the IRM may be administered, e.g., to a subject, but the active IRM compound may be regenerated by cleaving the labile bond.

As used herein, the following terms shall have the indicated meanings:

"Administer" and variations thereof refer to any manner of providing an IRM conjugate to immune cells for the intended purpose of generating an immune response. In many cases, an IRM conjugate may be administered to a subject such as, for example, a patient who is receiving the conjugate as a part of a prophylactic or therapeutic therapy. In other cases, an IRM conjugate may be administered to a cell culture in vitro.

"Agonist" refers to a compound that can combine with a receptor (e.g., a TLR) to induce a cellular activity. An agonist may be a ligand that directly binds to the receptor. Alternatively, an agonist may combine with a receptor indirectly by, for example, (a) forming a complex with another molecule that directly binds to the receptor, or (b) otherwise results in the modification of another compound so that the other compound directly binds to the receptor. An agonist may be referred to as an agonist of a particular TLR (e.g., a TLR6 agonist) or a particular combination of TLRs (e.g., a TLR 7/8 agonist—an agonist of both TLR7 and TLR8).

"Ameliorate" refers to any reduction in the extent, severity, frequency, and/or likelihood of a symptom or clinical sign characteristic of a particular condition.

"Antigen" refers to any substance that may be bound by an antibody in a manner that is immunospecific to some degree.

"Immune cell" refers to a cell of the immune system, i.e., a cell directly or indirectly involved in the generation or maintenance of an immune response, whether the immune response is innate, acquired, humoral, or cell-mediated.

"Immunomodulatory" and variations thereof refer to any increase or decrease (i.e., induction or inhibition) of immune activity.

"Induce" and variations thereof refer to any measurable increase in cellular activity. For example, induction of an immune response may include, for example, an increase in the production of a cytokine, activation, proliferation, or maturation of a population of immune cells, and/or other indicator of increased immune function.

"Inhibit" and variations thereof refer to any measurable reduction of cellular activity. For example, inhibition of a particular cytokine refers to a decrease in production of the cytokine. The extent of inhibition may be characterized as a percentage of a normal level of activity.

"IRM compound" refers generally to an immune response modifier compound that alters the level of one or more immune regulatory molecules, e.g., cytokines or co-stimulatory markers, when administered to an IRM-responsive cell. Representative IRM compounds include, for example, the small organic molecules, purine derivatives, small heterocyclic compounds, amide derivatives, and oligonucleotide sequences described above.

"IRM moiety" refers to that portion of an IRM conjugate that, as part of the conjugate, possesses little or no immunomodulatory activity, but when free possesses immunomodulatory activity. The IRM moiety may be, or be derived from, an IRM compound, but may, alternatively, be or be derived from some other immunomodulatory material. In some cases, the term "IRM moiety" may refer to an IRM compound prior to formation of the labile bond or after the labile bond has been cleaved and the IRM has been freed from the conjugate.

"Prophylactic" and variations thereof refer to a treatment that limits, to any extent, the development and/or appearance of a symptom or clinical sign of a condition.

"Selective" and variations thereof refer to having a differential or a non-general impact on biological activity. An agonist that selectively modulates biological activity through a particular TLR may be a TLR-selective agonist. TLR-selectivity may be described with respect to a particular TLR (e.g., TLR8-selective or TLR7-selective) or with respect to a particular combination of TLRs (e.g., TLR 7/9-selective).

"Sign" or "clinical sign" refers to an objective physical finding relating to a particular condition capable of being found by one other than the patient.

"Specific" and variations thereof refer to having a differential or a non-general affinity, to any degree, for a particular target.

"Symptom" refers to any subjective evidence of disease or of a patient's condition.

"Targeting moiety" refers to that portion of an immunomodulatory composition that possesses target-specific affinity. The targeting moiety may be, or be derived from, an antibody, but may, alternatively, be or be derived from a non-antibody protein or peptide, or non-protein material including, for example, small molecules and/or nanoparticles. In some cases, the term "targeting moiety" may refer to an uncoupled compound prior to coupling to, or after uncoupling from, an IRM moiety.

"Therapeutic" and variations thereof refer to a treatment that ameliorates one or more existing symptoms or clinical signs associated with a condition.

"Treat" or variations thereof refer to reducing, limiting progression, ameliorating, preventing, or resolving, to any extent, the symptoms or signs related to a condition.

As used herein, "a," "an," "the," "at least one," and "one or more" are used interchangeably. Thus, for example, a formulation comprising "an" IRM conjugate can be interpreted to mean that the formulation includes at least one IRM compound.

Also herein, the recitations of numerical ranges by endpoints include all numbers subsumed within that range (e.g., 1 to 5 includes 1, 1.5, 2, 2.75, 3, 3.80, 4, 5, etc.), unless otherwise indicated.

The IRM moiety may be, or be derived from, any suitable IRM compound. Generally, IRM compounds possess potent immunomodulating activity including but not limited to antiviral and antitumor activity. Certain IRMs modulate the production and secretion of cytokines. For example, certain IRM compounds induce the production and secretion of cytokines such as, e.g., Type I interferons, TNF-α, IL-1, IL-6, IL-8, IL-10, IL-12, MIP-1, and/or MCP-1. As another example, certain IRM compounds can inhibit production and secretion of certain $T_H2$ cytokines, such as IL-4 and IL-5. Additionally, some IRM compounds are said to suppress IL-1 and TNF (U.S. Pat. No. 6,518,265).

Certain IRMs are small organic molecules (e.g., molecular weight under about 1000 Daltons, preferably under about 500 Daltons, as opposed to large biological molecules such as proteins, peptides, nucleic acids, and the like) such as those disclosed in, for example, U.S. Pat. Nos. 4,689,338; 4,929,624; 5,266,575; 5,268,376; 5,346,905; 5,352,784; 5,389,640; 5,446,153; 5,482,936; 5,756,747; 6,110,929; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; 6,797,718; 6,818,650; and 7,7091, 214; U.S. Patent Publication Nos. 2004/0091491; 2004/0176367; and 2006/0100229; and International Publication Nos. WO 2005/18551, WO 2005/18556, WO 2005/20999, WO 2005/032484, WO 2005/048933, WO 2005/048945, WO 2005/051317, WO 2005/051324, WO 2005/066169, WO 2005/066170, WO 2005/066172, WO 2005/076783, WO 2005/079195, WO 2005/094531, WO 2005/123079, WO 2005/123080, WO 2006/009826, WO 2006/009832, WO 2006/026760, WO 2006/028451, WO 2006/028545, WO 2006/028962, WO 2006/029115, WO 2006/038923, WO 2006/065280, WO 2006/074003, WO 2006/083440, WO 2006/086449, WO 2006/091394, WO 2006/086633, WO 2006/086634, WO 2006/091567, WO 2006/091568, WO 2006/091647, WO 2006/093514, and WO 2006/098852.

Additional examples of small molecule IRMs include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329,381; and in WO 02/08905), certain 3-β-D-ribofuranosylthiazolo[4,5-d]pyrimidine derivatives (such as those described in U.S. Publication No. 2003/0199461), and certain small molecule immuno-potentiator compounds such as those described, for example, in U.S. Patent Publication No. 2005/0136065.

Other IRMs include large biological molecules such as oligonucleotide sequences. Some IRM oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other IRM nucleotide sequences lack CpG sequences and are described, for example, in International Patent Publication No. WO 00/75304. Still other IRM nucleotide sequences include guanosine- and uridine-rich single-stranded RNA (ssRNA) such as those described, for example, in Heil et al., *Science*, vol. 303, pp. 1526-1529, Mar. 5, 2004.

Other IRMs include biological molecules such as aminoalkyl glucosaminide phosphates (AGPs) and are described, for example, in U.S. Pat. Nos. 6,113,918; 6,303,347; 6,525,028; and 6,649,172.

Unless otherwise indicated, reference to a compound can include the compound in any pharmaceutically acceptable form, including any isomer (e.g., diastereomer or enantiomer), salt, solvate, polymorph, and the like. In particular, if a compound is optically active, reference to the compound can include each of the compound's enantiomers as well as racemic and scalemic mixtures of the enantiomers.

In some embodiments of the present invention, the IRM moiety may be, or be derived from, a compound that is an agonist of at least one TLR such as, for example, TLR7 or TLR8. The IRM may also in some cases be an agonist of TLR 9. In some embodiments of the present invention, the IRM compound may be a small molecule immune response modifier (e.g., molecular weight of less than about 1000 Daltons).

In some embodiments of the present invention, the IRM moiety may include a 2-aminopyridine fused to a five membered nitrogen-containing heterocyclic ring, or a 4-aminopyrimidine fused to a five membered nitrogen-containing heterocyclic ring.

The IRM moiety may be, or be derived from, a compound having a 2-aminopyridine fused to a five membered nitrogen-containing heterocyclic ring. Such compounds include, for example, imidazoquinoline amines including but not limited to substituted imidazoquinoline amines such as, for example, amide substituted imidazoquinoline amines, sulfonamide substituted imidazoquinoline amines, urea substituted imidazoquinoline amines, aryl ether substituted imidazoquinoline amines, heterocyclic ether substituted imidazoquinoline amines, amido ether substituted imidazoquinoline amines, sulfonamido ether substituted imidazoquinoline amines, urea substituted imidazoquinoline ethers, thioether substituted imidazoquinoline amines, hydroxylamine substituted imidazoquinoline amines, oxime substituted imidazoquinoline amines, 6-, 7-, 8-, or 9-aryl, heteroaryl, heterocyclyl, aryloxy or arylalkyleneoxy substituted imidazoquinoline amines, and imidazoquinoline diamines; tetrahydroimidazoquinoline amines including but not limited to amide substituted tetrahydroimidazoquinoline amines, sulfonamide substituted tetrahydroimidazoquinoline amines, urea substituted tetrahydroimidazoquinoline amines, aryl ether substituted tetrahydroimidazoquinoline amines, heterocyclic ether substituted tetrahydroimidazoquinoline amines, amido ether substituted tetrahydroimidazoquinoline amines, sulfonamido ether substituted tetrahydroimidazoquinoline amines, urea substituted tetrahydroimidazoquinoline ethers, thioether substituted tetrahydroimidazoquinoline amines, hydroxylamine substituted tetrahydroimidazoquinoline amines, oxime substituted tetrahydroimidazoquinoline amines, and tetrahydroimidazoquinoline diamines; imidazopyridine amines including but not limited to amide substituted imidazopyridine amines, sulfonamide substituted imidazopyridine amines, urea substituted imidazopyridine amines, aryl ether substituted imidazopyridine amines, heterocyclic ether substituted imidazopyridine amines, amido ether substituted imidazopyridine amines, sulfonamido ether substituted imidazopyridine amines, urea substituted imidazopyridine ethers, and thioether substituted imidazopyridine amines; 1,2-bridged imidazoquinoline amines; 6,7-fused cycloalkylimidazopyridine amines; imidazonaphthyridine amines; tetrahydroimidazonaphthyridine amines; oxazoloquinoline amines; thiazoloquinoline amines; oxazolopyridine amines; thiazolopyridine amines; oxazolonaphthyridine amines; thiazolonaphthyridine amines; pyrazolopyridine amines; pyrazoloquinoline amines; tetrahydropyrazoloquinoline amines; pyrazolonaphthyridine amines; tetrahydropyrazolonaphthyridine amines; and 1H-imidazo dimers fused to pyridine amines, quinoline amines, tetrahydroquinoline amines, naphthyridine amines, or tetrahydronaphthyridine amines.

In certain embodiments, the IRM moiety may be, or be derived from, an imidazonaphthyridine amine, a tetrahydroimidazonaphthyridine amine, an oxazoloquinoline amine, a thiazoloquinoline amine, an oxazolopyridine amine, a thiazolopyridine amine, an oxazolonaphthyridine amine, a thiazolonaphthyridine amine, a pyrazolopyridine amine, a pyrazoloquinoline amine, a tetrahydropyrazoloquinoline amine, a pyrazolonaphthyridine amine, or a tetrahydropyrazolonaphthyridine amine.

Suitable IRM moieties also may be, or be derived from, compounds such as, for example, the purine derivatives, imidazoquinoline amide derivatives, benzimidazole derivatives, adenine derivatives, aminoalkyl glucosaminide phosphates, small molecule immuno-potentiator compounds, and oligonucleotide sequences described above. In some embodiments, the IRM compound may be a compound identified as an agonist of one or more TLRs.

The second active moiety may be any moiety other than a second IRM moiety that possesses a biological activity. For example, the second active moiety may include an antigen or a targeting moiety.

Conjugates that include an antigen and an active IRM moiety are described, for example, in U.S. Patent Publication No. 2004/0091491. These conjugates can increase the immune response against the antigen by promoting the co-delivery of IRM compound and antigen to an antigen presenting cell.

Some embodiments of the present invention includes conjugates that include an antigen and an IRM moiety in which the IRM moiety is inactive until the labile bond is cleaved, releasing an active IRM moiety. Such conjugates may be useful for allowing an administered conjugate to reach a target tissue before inducing an immune response. This may provide a therapeutic benefit by inducing a more highly localized antigen-specific immune response. The IRM moiety may be kept inactive until the conjugate reaches the targeted tissue where the antigen-specific immunotherapy is needed, thereby reducing, even preventing, a systemic immune response against the antigen that could be induced by an active IRM moiety before the conjugate is able to reach its target tissue.

In certain embodiments, the second active moiety may be a targeting moiety—i.e., a moiety that acts to target the delivery, or cause the selective retention, of the conjugate to a particular tissue or cell population. The particular nature of a targeting moiety may be determined, to some extent, by the identity and nature of the intended target. For example, a suitable targeting moiety may actively provide directed binding to a target, as in an antibody directed against the antigenic portion of a tumor, target cell, target tissue, or target organ. Active targeting can also be achieved by exploiting receptor-ligand affinity. In other cases, the targeting moiety may provide passive retention of the conjugate in a target. Passive retention may be accomplished by exploiting differences in hydrophobicity/hydrophilicity, vascular porosity, etc. of target vs. non-target environments.

A targeting moiety may be any material that can provide targeted delivery of a conjugate. In many embodiments, the targeting portion may provide immunospecific targeting, i.e., may be a sufficient portion of an immunoglobulin (i.e., an antibody) to promote immunospecific binding of the composition to a target antigen. However, the invention may be practiced using non-immunoglobulin targeting materials as well such as, for example, receptor ligands such as, for example, hormones (natural or synthetic), lipids, etc.

In some cases, a targeting moiety may be an antibody or be derived from an antibody (i.e., at least enough of the immunospecific portion of an antibody—e.g., enough of a light chain—to provide some degree of immunospecificity. However, in other cases, a targeting moiety may be, or be derived from, an agent that recognizes at least a portion of a tumor-specific marker such as, for example, a ligand that binds to a receptor that is, to some extent, specifically expressed by the target cell population. In such a case, the receptor may be considered a tumor-specific marker. Other tumor-specific targeting moieties include, for example, certain non-protein materials such as, for example, nanoparticles and certain small molecules.

Conjugates designed for use treating tumors may include a tumor-specific targeting moiety and a labile bond that is selected because it is more likely, more quickly, or more efficiently cleaved in a tumor environment than in the systemic environment. The microenvironment of tumors is often characterized as having low oxygen tension, low extracellular pH, and low glucose concentration. Labile bonds that can exploit one or more of these microenvironmental conditions, e.g., low pH, may make a labile bond particularly well suited for use in a conjugate designed for treating the tumor.

Nanoparticles can possess tumor-specific targeting activity in at least two ways. First, the nanoparticle may be coated with a targeting moiety that directs the nanoparticle to a tumor. Methods for attaching targeting moieties (e.g., antibodies, receptor ligands, etc.) are well known. Second, nanoparticles may provide passive retention within a tumor target. Nanoparticles having a diameter of from about 50 nm to about 200 nm may be delivered systemically and reside in bloodstream until they reach tumor vasculature. Localized changes in the porosity or permeability of the circulatory system can permit the nanoparticles to escape the bloodstream, leave the circulatory system, and be deposited in the vicinity of the tumor. Thus, a conjugate of the invention that includes a nanoparticle as a targeting moiety may allow systemic administration of the conjugate, selective retention of the conjugate at a tumor, and a delay in the onset of IRM activity until conjugate has had the opportunity to reach, and be retained at, the tumor site.

One example of a small molecule moiety that can provide tumor-specific targeted delivery of an IRM moiety is bis-phosphonate. Bis-phosphonate functionality imparts high affinity, long-term association to the hydroxyapetite components of bone. Bis-phosphonates are known to be useful for targeted delivery and sequestering of diagnostic and/or therapeutic agents in bone. For example, bis-phosphonate drugs are used diagnostically for the delivery of bone imaging agents and therapeutically in osteoporosis, tumor osteolysis, and bone metastasis. An IRM/bis-phosphonate conjugate could provide a depot of IRM within a common site of metastasis.

Leuteinizing hormone releasing hormone (LHRH) receptors are significantly elevated on breast cancer, prostate cancer, endometrial cancer, ovarian cancer, and melanoma cells. Thus, ligands of LHRH receptors may be used as a targeting moiety in a conjugate to provide tumor-specific targeted delivery of the IRM moiety to a tumor site. In animal models for the human cancers noted above, LHRH-directed therapeutics selectively home to the affected tissues. Coupling an IRM to a ligand of the LHRH receptor (e.g., LHRH or a synthetic analog) can provide targeted delivery of the IRM to tumor cells of these cancers, thereby concentrating the IRM at the site of the tumor and increasing the therapeutic index over that observed with the IRM compound alone. In studies comparing free Dox to LHRH-conjugated Dox, approximately 200 times more free Dox was required to demonstrate an antitumor activity equal to the LHRH conjugate. Suitable LHRH receptor ligands could include LHRH decapeptide, an analog with agonist or antagonist activity, or a small molecule receptor ligand.

LHRH receptor is known to be overexpressed on many tumor cells (e.g., breast, prostate, melanoma) compared to normal organ tissues. Thus, a single IRM-LHRH receptor ligand conjugate could be useful for treating more than one type of cancer.

Folic acid receptor ligands also may be useful as targeting moieties that provide tumor-specific targeted delivery of the IRM moiety. The expression of folic acid receptors is increased on the surface of many tumor cells. Once again, coupling a folic acid receptor ligand to an IRM moiety can result in selective accumulation of the IRM at a tumor site, reducing systemic availability of the IRM moiety, and increasing the therapeutic index of the IRM moiety. Suitable folic acid receptor ligands include folic acid, an analog with agonist or antagonist activity, or a small molecule receptor ligand.

In some alternative embodiments, an IRM moiety may be conjugated to a dendritic cell targeting moiety. The targeting moiety may be an antibody (e.g., an anti-DC antibody) or a non-antibody ligand that recognizes a DC-specific marker.

Suitable DC-specific markers may include, for example, a co-stimulatory marker such as, for example, any member of the TNFR Superfamily (e.g., CD40), CD70, CD80, CD86, B7-CD, B7.1, B7.2, etc. A conjugate that includes a targeting moiety that recognizes a co-stimulatory marker may be used to deliver two DC-activating stimuli (i.e., IRM moiety and co-stimulation) in a single chemical entity.

As used herein, an anti-DC antibody refers to an antibody that recognizes a dendritic cell antigen. A suitable dendritic cell targeting moiety may bind to any antigen that is differentially expressed, either qualitatively or quantitatively, by dendritic cells. Suitable dendritic cell targeting moieties may bind to such antigens as, for example, DEC205, BDCA-1, BDCA-2, BDCA-3, BDCA-4, DC-SIGN, L-SIGN, HLR-DR, CD11c, CD13, CD14, CD21, CD33, CD35, CD123, C-type lectins, integrins (e.g., $\alpha 4$, $\alpha 6$, $\alpha 1\beta 1$), and/or any one of the Toll-like receptors (TLRs), etc.

Regardless of whether the targeting moiety recognized a DC-specific marker or antigen, conjugating the IRM moiety to the targeting moiety can limit systemic availability of the IRM moiety, even when administered via a systemic delivery route. Moreover, the conjugate, and thus the IRM moiety, may be concentrated in the vicinity of dendritic cells, thereby maturing and activating dendritic cells more effectively. Dendritic cells activated at the site of a tumor—or even inside a tumor mass—may be able to utilize a tumor antigen present on the surface of the tumor cells to initiate an immune response against the tumor. This method could provide a generalized anti-tumor therapy without the need for tumor-specific antibodies.

In other alternative embodiments, an IRM moiety may be conjugated to an anti-macrophage targeting moiety. Macrophages are often localized in the vicinity of tumor cells. Thus, again, systemic availability of the IRM moiety can be limited, and the IRM moiety may be concentrated in the vicinity of the target cells (i.e., macrophages), thereby activating macrophages more efficiently. Activated macrophages are known to possess anti-tumor activity. Thus, this method could provide a generalized tumor therapy without the need for tumor-specific antibodies.

In other alternative embodiments, an IRM moiety may be conjugated to a target specific moiety that recognizes a surface antigen on a cell type that can directly kill tumor cells such as, for example, $CD8^+$ cytotoxic T cells, NK cells, or NKT cells. Once again, even if the conjugate is administered systemically, the IRM moiety may be concentrated in the vicinity of the tumor-killing cells, thereby (a) activating tumor-killing cells more effectively, and/or (b) limiting the systemic availability of the IRM moiety. Tumor-killing cells activated at the site of a tumor—or even inside a tumor mass—may be able to utilize a tumor antigen present on the surface of the tumor cells to initiate an immune response against the tumor. This method could provide a generalized tumor therapy without the need for tumor-specific antibodies.

In other alternative embodiments, the IRM moiety may be conjugated to a targeting moiety that recognizes, for example, an endothelial target. Significant differences exist in the endothelium environments of tumor masses compared to normal capillary beds. Differences exist, for example, in the identity and extent to which certain endothelial surface proteins, adhesion molecules (e.g., integrins), extracellular matrix proteins, growth factor receptors, etc. are expressed. These differences can be exploited to target delivery of an IRM moiety to tumor-related endothelium. Some reagents that specifically target such differences have been demonstrated to be useful as anti-angiogenic therapies. Conjugating such an agent, as a targeting moiety, to an IRM moiety can combine two effective anti-tumor therapies: immunotherapy and anti-angiogenesis therapy.

Suitable anti-angiogenesis reagents include, for example, anti-CD105 antibodies (CD105 is overexpressed in tumor endothelium), anti-ED-B antibodies (ED-B is a fibronectin isoform found in tumor masses), peptides recognized by endothelial integrins associated with tumors, and growth factors whose receptors are upregulated on tumor endothelium (e.g., vascular endothelial growth factor).

The use of anti-angiogenic reagents in this way may offer the promise of combined anti-angiogenesis and immunotherapy. Additionally, targeted delivery of an IRM to the tumor endothelium, as opposed to the tumor itself, may provide more effective long-term treatment since, generally, the endothelium is a less mutagenic tissue than a tumor mass. Therefore, therapy directed toward the endothelium may be far less likely to cause drug resistance. Also, a therapy directed toward the endothelium may be effective against virtually any vascularized tumor (e.g., breast cancer, prostate cancer, lung cancer) without the need for tumor-specific reagents.

In some embodiments, a targeting moiety may include an immunoglobulin or at least a functional portion of an immunoglobulin. Because immunoglobulins are proteins, it is understood that modifications can be made to a particular immunoglobulin without rendering the modified immunoglobulin unsuitable for use as a targeting moiety. For example, one or more portions of the immunoglobulin amino acid sequence may be deleted or substituted, or additional amino acids may be added to an immunoglobulin, and the immunoglobulin can still retain sufficient immunospecific character to be suitable for use as a targeting moiety. Examples of suitable antibodies are described, for example, in U.S. Patent Publication No. 2006/0142202.

The labile bond may be any covalent bond that is readily cleaved in vivo and that links the second active moiety to the IRM moiety at a location on the IRM moiety that causes a substantial reduction in the immunomodulatory activity of the IRM moiety. When the labile bond is intact—i.e., when the IRM moiety is linked to the second active moiety—the IRM moiety will have substantially reduced immunomodulatory activity. When the labile bond is cleaved, however, a free and active IRM moiety—now a free IRM compound—is released and capable of inducing an immune response.

In some cases, the reduction in immunomodulatory activity may be due primarily to the location of the labile bond attachment on the IRM moiety—e.g., the 4-amine of certain imidazoquinoline derivatives. In these cases, the reduction of immunomodulatory activity may be independent of the identity, chemical nature, or physical nature of the particular substitution. Rather, in some cases, the reduction in immunomodulatory activity may be due solely to the presence of a covalent substitution at that position on the IRM moiety.

In other cases, the reduction in immunomodulatory activity may be due primarily to the identity and nature—e.g., size and/or steric nature—of the substitution. In these cases, the substitution may reduce the immunomodulatory activity of the IRM moiety by, for example, covering the portion of the IRM moiety that binds to receptors and initiates a cell signaling cascade that results in an immune response. In such cases, the location of the labile bond attachment on the IRM moiety may be less important, other than to provide the second active moiety in a location that allows the second active moiety to inhibit the immunomodulating activity of the IRM moiety.

The labile bond is, in all cases, readily cleaved in vivo, so that the link between the IRM moiety and the second active moiety may be broken, thereby releasing free and active IRM compound that is capable of contacting immune cells and inducing an immune response.

Examples of suitable labile bonds include, but are not limited to, an amide bond, a carbamate bond, an amidine bond, an ester bond, a disulfide bond, or the amide bond of a peptide unit used with or without a self-immolative spacer, such as those described in the literature (Toki, B. E. et al., *J. Org. Chem.*, 2002, 67, 1866-1872; Jeffrey, S. C. et al., *J. Med. Chem.*, 2005, 48, 1344-1358; Sun, M. M. C. et al., *Bioconjugate Chem.* 2005, 16, 1282-1290) and International Publication Nos. WO 2005/082023 and WO 2004/0101957.

In some embodiments, the labile bond is selected from the group consisting of an amide bond, a carbamate bond, an amidine bond, an ester bond, and a disulfide bond. In other embodiments, the labile bond is selected from the group consisting of an amide bond, a carbamate bond, and an amidine bond. In some embodiments, the labile bond is an amide bond.

The labile bond is readily cleaved in vivo. The cleavage may occur by various mechanisms, such as through a chemical (e.g. hydrolysis at physiological pH or hydrolysis at the lower pH environment found within certain tumors) or enzymatic (e.g. reaction with an esterase) biotransformation.

Preparation of IRM Conjugates

IRM conjugates of the invention can be prepared using the general method illustrated in Reaction Scheme I, wherein IRM, second active moiety (SAM), and labile bond (LB) are as described above, p is an integer from 1 to 20, $FG_A$ and $FG_B$ are functional groups described in greater detail below and specifically exemplified in Table A below, and Linker A, Linker B, and Linker C are defined below.

TABLE A

| Linkage | Bond | $FG_A$ | $FG_B$ |
|---|---|---|---|
| 1a | 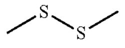 | 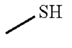 | 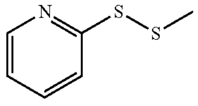 |
| 1b | 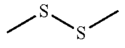 | 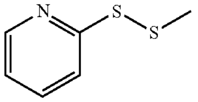 | 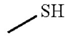 |
| 2a | 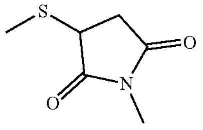 | 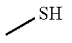 | 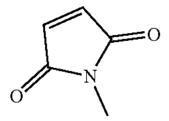 |
| 2b | 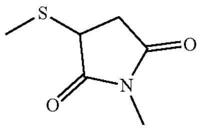 | 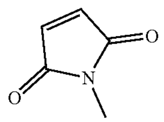 | 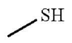 |
| 3a | 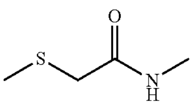 | 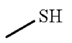 | 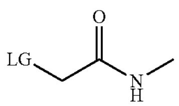 |
| 3b | 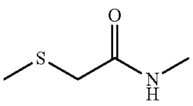 | 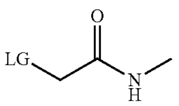 | 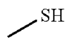 |
| 4a | 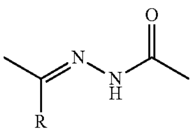 | 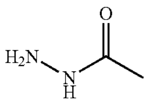 | 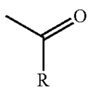 |
| 4b | 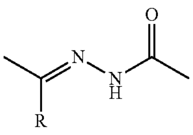 | 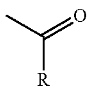 | 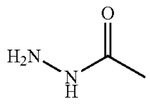 |

TABLE A-continued
| Linkage | Bond | $FG_A$ | $FG_B$ |
|---|---|---|---|
| 5a | 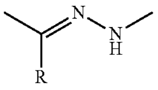 | 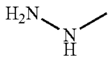 | 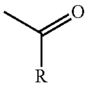 |
| 5b | 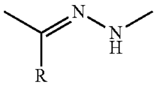 | 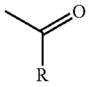 | 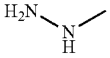 |
| 6a | 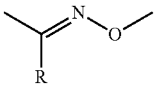 | 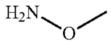 | 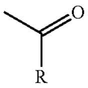 |
| 6b | 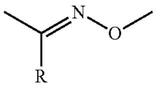 | 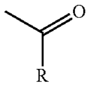 | 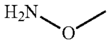 |
| 7 | 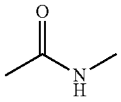 | 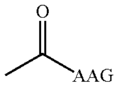 | 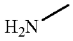 |
| 8 | 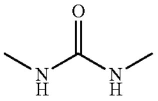 | 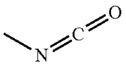 | 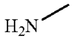 |
| 9 | 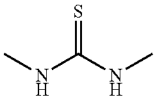 | 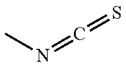 | 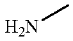 |
| 10 | 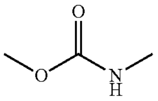 | 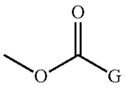 | 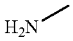 |
| *11 | 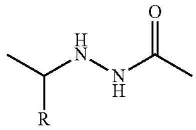 | — | — |
| *12 | 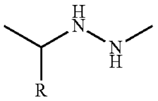 | — | — |
| *13 | 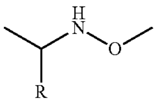 | — | — |
| 14 | 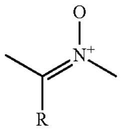 | 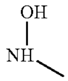 | 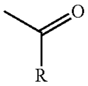 |

TABLE A-continued

| Linkage | Bond | $FG_A$ | $FG_B$ |
|---|---|---|---|
| 15 | 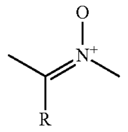 | 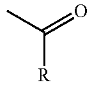 | 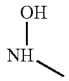 |

LG is a leaving group selected from Cl, Br, I, O-mesyl, and O-Tosyl.
AAG is an acid activating group selected from an EDC activated acid; NHS, sNHS, 4-nitrophenyl, chloride, bromide, anhydride or mixed anhydride, pentafluorophenyl ester, and tetrafluorophenyl ester.
G is selected from Cl, O—CH(Cl)$CCl_3$, O-(4-nitrophenyl), NHS, and imidazole.
*Linkages 11-13 obtained by reduction of linkages 4-6.

Linker A is an organic moiety that links the IRM with functional group $FG_A$.

Suitable linkers include divalent organic moieties of the formulas —X—, —X—Y—X—, and —X—Y—X—Y—X— wherein X and Y are as defined below. Examples of such linkers include —$C_{1-10}$-alkylene-, —$C_{1-10}$alkylene-arylene-, arylene-$C_{1-10}$alkylene-, —$C_3$-$C_8$-heterocyclene-, —$C_{1-10}$alkylene-$C_3$-$C_8$-heterocyclene-, and —$C_3$-$C_8$-heterocyclene-$C_{1-10}$-alkylene-. Other suitable linkers include —$(CH_2CH_2O)_q$— and —$(CH_2CH_2O)_q$—$CH_2$— wherein q is an integer from 1 to 10. Suitable linkers also include those discussed in greater detail in the Reaction Schemes below and those specifically exemplified in the EXAMPLES below.

Linker B is an organic moiety that links the SAM with functional group $FG_B$.

Suitable linkers include, but are not limited to, divalent organic moieties of the formulas —X—, —X—Y—X—, —Z—X—, and —Z—X—Y—X— wherein X, Y, and Z are as defined below. Examples of such linkers include —$C_{1-10}$-alkylene-, —O—($C_{1-8}$alkylene)-arylene, —$C_{1-10}$alkylene-arylene-, arylene-$C_{1-10}$alkylene-, —$C_3$-$C_8$-heterocyclene-, —$C_{1-10}$alkylene-$C_3$-$C_8$-heterocyclene-, and —$C_3$-$C_8$-heterocyclene-$C_{1-10}$-alkylene-. Other suitable linkers include —$(CH_2CH_2O)_q$— and —$(CH_2CH_2O)_q$—$CH_2$— wherein q is an integer from 1 to 10.

Linker C is an organic moiety that links one or more IRMs with the SAM. Linker C includes the linkage formed when $FG_A$ and $FG_B$ react with each other. Examples of such linkages include those in Table A above. The structure of the Linker C is determined by the structures of Linker A and Linker B and by the particular $FG_A$ and $FG_B$ groups attached to the IRM or the SAM.

In step (1) of Reaction Scheme I, a second active moiety (SAM) is modified to provide a functionalized moiety of Formula II using conventional methods.

Functionalized moieties of Formula II can be prepared using a heterobifunctional crosslinker. The general definition of a heterobifunctional crosslinker is as follows "... a heterobifunctional cross-linking agent includes two different reactive groups at either end, and an organic cross-bridge of various length and composition." (Hermanson, G. (1996), *Bioconjugate Techniques*, Academic Press, Chapter 5 "Heterobifunctional Cross-Linkers", page 229). Useful functional groups often found on SAMs include, but are not limited to, amines (—$NH_2$), thiols (—SH), and aldehydes (—CHO), which can be derivatized with heterobifunctional crosslinkers that contain, respectively, amine reactive groups, thiol reactive groups, and aldehyde reactive groups. The other reactive group on the heterobifunctional crosslinker is chosen such that it provides the desired functional group $FG_B$ in a functionalized moiety of Formula II. Many heterobifunctional cross-linkers are known (Hermanson, G. (1996), *Bioconjugate Techniques*, Academic Press, Chapter 5 "Heterobifunctional Cross-Linkers", pages 229-285) and many are commercially available (Pierce Biotechnology, Inc. of Rockford, Ill. and other suppliers). In addition, heterobifunctional crosslinkers can also be synthesized using conventional methods.

Functional groups on a heterobifunctional crosslinker that can react with amines on the SAM include, but are not limited to, any functional group $FG_A$ that can react with an amine as shown in Table A. Preferred functional groups include activated carboxylic acids such N-hydroxysuccinimide esters or sulfo-N-hydroxysuccinimide esters, isocyanates, and thioisocyanates. Examples of useful heterobifunctional crosslinkers that can react with amines and provide $FG_B$ as a maleimide are the following: sulfo-N-succinimidyl 4-(maleimidomethyl)cyclohexane-1-carboxylate, sodium salt (Sulfo SMCC)

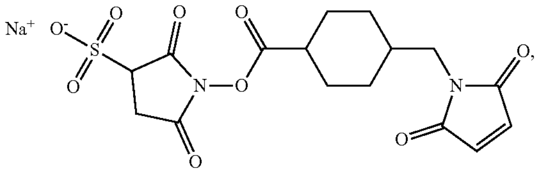 [SMILES: [Na+] ; O=C(ON1C(=O)CC(S(=O)(=O)[O-])C1=O)C1CCC(CN2C(=O)C=CC2=O)CC1]

N-(γ-maleimidobutyryloxy)sulfosuccinimide ester (Sulfo-GMBS)

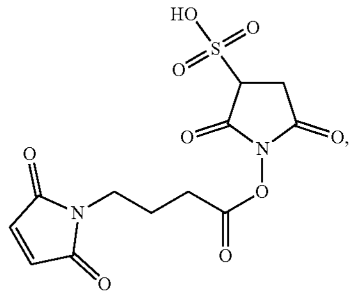 [SMILES: O=C(CCCN1C(=O)C=CC1=O)ON1C(=O)CC(S(=O)(=O)O)C1=O]

succinimidyl-[(N-maleimidopropionamido)-tetraethyleneglycol] ester (NHS-$PEO_4$-Maleimide)

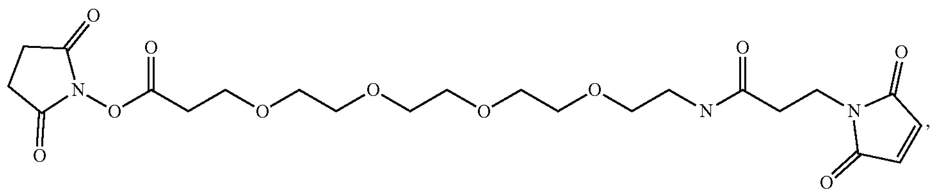 [SMILES: O=C(CCN1C(=O)C=CC1=O)NCCOCCOCCOCCOCCC(=O)ON1C(=O)CCC1=O]

and succinimidyl-[(N-maleimidopropionamido)-octaethyleneglycol] ester, (NHS-$PEO_8$-Maleimide)

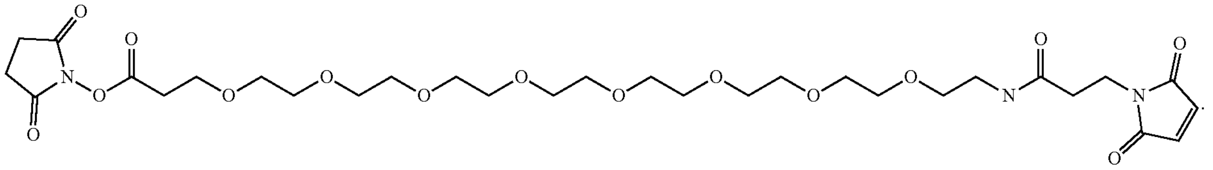 [SMILES: O=C(CCN1C(=O)C=CC1=O)NCCOCCOCCOCCOCCOCCOCCOCCOCCC(=O)ON1C(=O)CCC1=O]

An example of a useful heterobifunctional crosslinker that can react with an amine and provide $FG_B$ as an bromo acetyl group is N-succinimidyl 3-(bromoacetamido)propionate (SBAP),

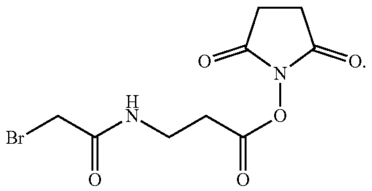 [SMILES: O=C(CBr)NCCC(=O)ON1C(=O)CCC1=O]

An example of a useful heterobifunctional crosslinker that can react with an amine and provide $FG_B$ as a 2-pyridyl disulfide is 4-succinimidyloxycarbonyl-methyl-α-(2-pyridyldithio)toluene (SMPT),

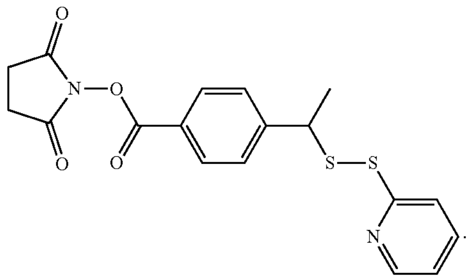 [SMILES: CC(SSc1ccccn1)c1ccc(C(=O)ON2C(=O)CCC2=O)cc1]

In general, when the SAM contains a thiol group, the SAM may be treated with a reagent such as N-ethylmaleimide prior to treatment with a heterobifunctional crosslinker that installs $FG_B$ as a thiol reactive group. This prevents dimerization/oligomerization of the SAM of Formula II.

In addition, a useful reagent that can react with amines in a SAM to install a thiol as $FG_B$ in a functionalized moiety of Formula II is Traut's reagent (2-iminothiolane hydrochloride),

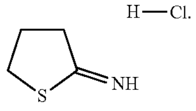

In some embodiments the SAM may contain a thiol that can react with a heterobifunctional crosslinker in step (1) of Reaction Scheme I to provide a functionalized moiety of Formula II. Heterobifunctional crosslinkers that are reactive toward thiols may contain, but are not limited to, any functional group $FG_A$ that can react with a thiol as shown in Table A. Preferred functional groups include activated disulfides such as a 2-pyridyl disulfide and a methyl sulfonyl disulfide, maleimides, and bromo or iodo acetyl groups. Some examples of useful heterobifunctional cross-linkers that can react with thiols and provide $FG_B$ as a hydrazide are [N-ε-maleimidocaproic acid]hydrazide (EMCH)

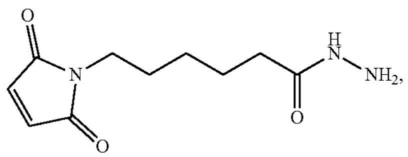 [SMILES: NNC(=O)CCCCCN1C(=O)C=CC1=O]

[N-ε-maleimidoundecanoic acid]hydrazide (KMUH)

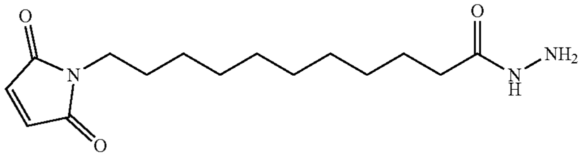 [SMILES: NNC(=O)CCCCCCCCCCN1C(=O)C=CC1=O]

3-(2-pyridyldithio)propionyl hydrazide (PDPH)

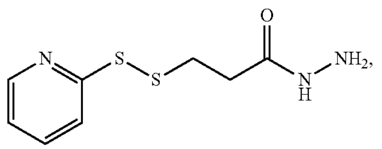 [SMILES: NNC(=O)CCSSc1ccccn1]

and 4-(maleimidomethyl)cyclohexane-1-carboxyl-hydrazide, trifluoracetic acid (SMCC-Hydrazide, TFA),

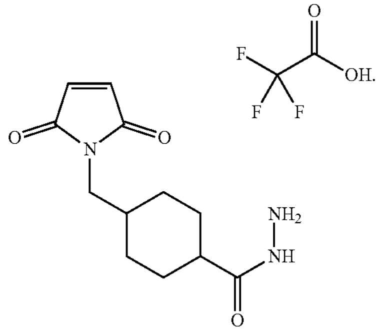 [SMILES: NNC(=O)C1CCC(CN2C(=O)C=CC2=O)CC1 ; O=C(O)C(F)(F)F]

In some embodiments, the SAM will contain an aldehyde that can react can react with a heterobifunctional crosslinker in step (1) of Reaction Scheme I to provide a functionalized moiety of Formula II. Functional groups on a heterobifunctional cross-linker that can react with an aldehyde on the SAM include, but are not limited to, any functional group $FG_A$ that can react with an aldehyde as shown in Table A. Useful functional groups include hydrazines (—$NHNH_2$), hydrazides (—$C(O)NHNH_2$), amines (—$NH_2$), hydroxyl amines (—NHOH), and O-substituted hydroxylamines (—O—$NH_2$). Examples of useful heterobifunctional cross-linkers that can react with aldehydes and provide $FG_B$ as a maleimide include EMCH, KMUH, and SMCC-Hydrazide. A useful heterobifunctional crosslinker that can react with aldehydes and provide $FG_B$ as a 2-pyridyl disulfide is PDPH. A functionalized moiety of Formula II that contains $FG_B$ as a 2-pyridyl disulfide can be reduced using known methods to provide $FG_B$ as a thiol.

Although not illustrated, in some embodiments the SAM may be used without the incorporation of Linker B. For example, a SAM that contains a functional group $FG_B$, can react with a functionalized IRM of Formula III to form a IRM-SAM Conjugate of Formula I. Useful functional groups $FG_B$ on the SAM include, but are not limited to, amines (—$NH_2$), thiols (—SH), and aldehydes (—CHO). When the SAM is a protein, it may contain cysteine or lysine amino acid residues that contain, respectively, thiols and amines. In some instances, useful functional groups $FG_B$ may be generated easily on the SAM. For example, carbohydrate residues on a glycoprotein can be oxidized using sodium periodate to form reactive aldehydes (Hermanson, G. (1996), *Bioconjugate Techniques*, Academic Press, p. 114). Furthermore, disulfide bonds in a protein can be reduced using a variety of reducing agents (Hermanson, G. (1996), *Bioconjugate Techniques*, Academic Press, p. 76) to form thiols.

In step (2) of Reaction Scheme I, an IRM is modified to provide a functionalized IRM of Formula III.

Functionalized IRMs of Formula III can be prepared using a heterobifunctional crosslinker employing a similar strategy to that described in step (1) above. Useful functional groups on the IRM that may be modified by a heterobifunctional crosslinker include, but are not limited to, amino, hydroxyl, and thiol groups. The heterobifunctional crosslinker is selected such that it provides the desired labile bond and the desired $FG_A$. Examples of useful heterobifunctional crosslinkers that can react with an amino group in the IRM include N-succinimidyl 3-(2-pyridyldithio)propionate and N-succinimidyl-3-maleimidopropionate, which yield functionalized IRMs of Formula III where the labile bond is an amide bond and $FG_A$ is pyridyldisulfide and maleimide respectively.

As described in greater detail below, functionalized IRMs of Formula III may be synthesized by means other than employing a heterobifunctional crosslinker. These alternative methods can provide linkers that cannot be obtained using commercially available heterobifunctional crosslinkers and may provide IRM conjugates having enhanced physical and/or biological properties as compared to those conjugates prepared using the commercially available heterobifunctional crosslinkers. The linker's length, bulk, rigidity or flexibility, and hydrophobicity or hydrophilicity can be optimized for each IRM conjugate of Formula I.

In step (3) of Reaction Scheme I, a functionalized SAM of Formula II is reacted with a functionalized IRM of Formula III to provide an IRM conjugate of Formula I using conventional methods. For example, the reaction can be carried out by adding a solution of the functionalized IRM of Formula III in a suitable solvent such as dimethyl sulfoxide (DMSO) or N,N-dimethylformamide (DMF) to a solution of a functionalized SAM of Formula II in a suitable solvent such as phosphate buffered saline (PBS). The reaction can be carried out at ambient temperature. The resulting IRM conjugate of Formula I can be purified using conventional methods such as, for example, size exclusion chromatography.

The functionalized SAM of Formula II and the functionalized IRM of Formula III are selected such that functional groups $FG_A$ and $FG_B$ react with each other to form a new covalent bond in the IRM conjugate of Formula I.

In some embodiments, $FG_A$ is an electrophilic group that is reactive to $FG_B$, which is a nucleophilic group. Useful electrophilic groups in include, but are not limited to, Michael acceptors such as maleimides, vinylsulfones, and acrylic acid derivatives; activated disulfides such as pyridyldisulfide and methyl sulfonyl disulfide; activated carboxylic acids such as N-hydroxysuccinimide ester, sulfo-N-hydroxysuccinimide ester, 4-nitrophenyl ester, acid chlorides, acid bromides, acid anhydrides, pentafluorophenyl ester, and tetrafluorophenyl ester; haloacetyl groups such as iodo-, bromo-, and chloroacetyl; activated carbonates such as succinimidyl carbonate, chloroformate (—OC(O)Cl), and carbonates of the formula —OC(O)—O—$CH(Cl)CCl_3$ and —OC(O)—O-(4-nitrophenyl); isocyanates; thioisocyanates; aldehydes; and ketones. Useful nucleophilic groups in $FG_B$ include, but are not limited to, thiols (—SH), hydrazines (—$NHNH_2$), hydrazides (—$C(O)NHNH_2$), amines (—$NH_2$), hydroxyl amines (—NHOH), and O-alkyl-hydroxylamines (—O—$NH_2$).

In some embodiments, $FG_A$ is a nucleophilic group that is reactive to $FG_B$, which is an electrophilic group.

Reaction Scheme I

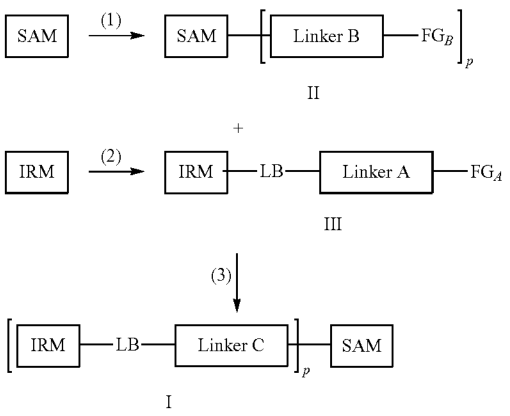

In some embodiments, IRM conjugates of the invention can be prepared using the general method illustrated in Reaction Scheme II, wherein SAM, $FG_A$, $FG_B$, Linker A, Linker B, Linker C, and p are as defined above; $FG_C$ is selected from the group consisting of

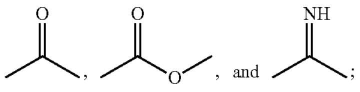

and $R_A$ and $R_B$ are each independently selected from the group consisting of:

hydrogen, halogen, alkyl, alkenyl, alkoxy, alkylthio, and

—$N(R_9)_2$;

or when taken together, $R_A$ and $R_B$ form a fused aryl ring or heteroaryl ring containing one heteroatom selected from the group consisting of N and S wherein the aryl or heteroaryl ring is unsubstituted or substituted by one or more R groups, or substituted by one $R_3$ group, or substituted by one $R_3$ group and one R group;

or when taken together, $R_A$ and $R_B$ form a fused 5 to 7 membered saturated ring, optionally containing one heteroatom selected from the group consisting of N and S, and unsubstituted or substituted by one or more R groups;

R is selected from the group consisting of:

halogen, hydroxy, alkyl, alkenyl, haloalkyl, alkoxy, alkylthio, and

—$N(R_9)_2$;

$R_1$ is selected from the group consisting of:

—$R_4$,

—X—$R_4$,

—X—Y—$R_4$,

—X—Y—X—Y—$R_4$, and

—X—$R_5$;

$R_2$ is selected from the group consisting of:

—$R_4$,

—X—$R_4$,

—X—Y—$R_4$, and

—X—$R_5$;

$R_3$ is selected from the group consisting of:

—Z—$R_4$,

—Z—X—$R_4$,

—Z—X—Y—$R_4$,

—Z—X—Y—X—Y—$R_4$, and

—Z—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:

—O—,

—$S(O)_{0-2}$—,

—$S(O)_2$—$N(R_8)$—,

—$C(R_6)$—,

—$C(R_6)$—O—,

—O—$C(R_6)$—,

—O—C(O)—O—,

—$N(R_8)$-Q-,

—$C(R_6)$—$N(R_8)$—,

—O—$C(R_6)$—$N(R_8)$—,

—$C(R_6)$—$N(OR_9)$—,

—O—$N(R_8)$-Q-,

—O—N═$C(R_4)$—,

—C(═N—O—$R_8$)—,

—CH(—N(—O—$R_8$)-Q-$R_4$)—,

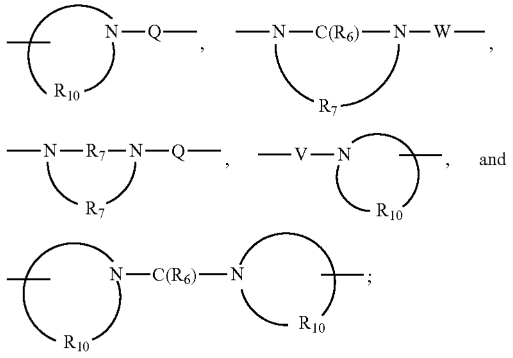

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

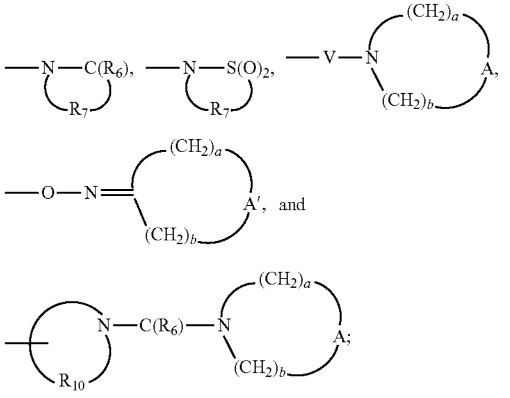

$R_6$ is selected from the group consisting of $=O$ and $=S$;

$R_7$ is $C_{2-7}$ alkylene;

$R_8$ is selected from the group consisting of hydrogen, alkyl, alkoxyalkylenyl, hydroxyalkylenyl, arylalkylenyl, and heteroarylalkylenyl;

$R_9$ is selected from the group consisting of hydrogen and alkyl;

$R_{10}$ is $C_{3-8}$ alkylene;

A is selected from the group consisting of —O—, —C(O)—, $—S(O)_{0-2}—$, and $—N(R_4)—$;

A' is selected from the group consisting of —O—, $—S(O)_{0-2}—$, $—N(\text{-}Q\text{-}R_4)—$, and $—CH_2—$; Q is selected from the group consisting of a bond, $—C(R_6)—$, $—C(R_6)—C(R_6)—$, $—S(O)_2—$, $—C(R_6)—N(R_8)—W—$, $—S(O)_2—N(R_8)—$, $—C(R_6)—O—$, $—C(R_6)—S—$, and $—C(R_6)—N(OR_9)—$;

V is selected from the group consisting of $—C(R_6)—$, $—O—C(R_6)—$, $—N(R_8)—C(R_6)—$, and $—S(O)_2—$;

W is selected from the group consisting of a bond, —C(O)—, and $—S(O)_2—$; and a and b are independently integers from 1 to 6 with the proviso that a+b is ≤7.

In Reaction Scheme II, a functionalized IRM of Formula IIIa, which is a subgenus of Formula III, is reacted with a functionalized SAM of Formula II to provide an IRM conjugate of Formula Ia, which is a subgenus of Formula I. The reaction can be carried out as described for step (3) of Reaction Scheme I.

Functionalized IRMs of Formula IIIa can be prepared using the general methods described in step (2) of Reaction Scheme I and using the methods described in greater detail below.

Functionalized SAMs of Formula II can be prepared as described in step (1) of Reaction Scheme I.

Reaction Scheme II

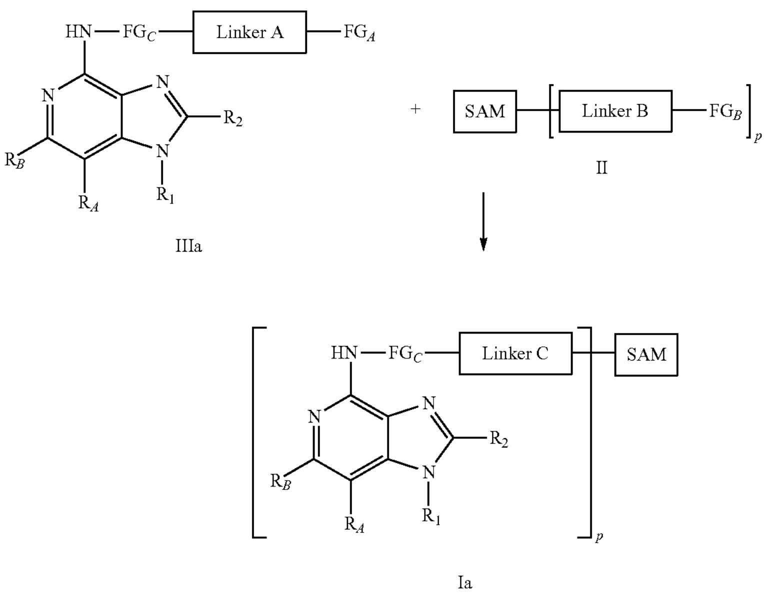

For certain embodiments, the IRM conjugate is of the Formula Ia.

In some embodiments, conjugates of the invention can be prepared using the general method illustrated in Reaction Scheme III, wherein SAM, $FG_A$, $FG_B$, $FG_C$, Linker A, Linker B, Linker C, $R_A$, $R_B$, $R_2$, and p are as defined above.

In Reaction Scheme III, a functionalized IRM of Formula IIIb, which is a subgenus of Formula III, is reacted with a functionalized SAM of Formula II to provide an IRM conjugate of Formula Ib, which is a subgenus of Formula I. The reaction can be carried out as described for step (3) of Reaction Scheme I.

Functionalized IRMs of Formula IIIb can be prepared using the general methods described in step (2) of Reaction Scheme I and using the methods described in greater detail below.

Functionalized SAMs of Formula II can be prepared as described in step (1) of Reaction Scheme I.

Reaction Scheme III

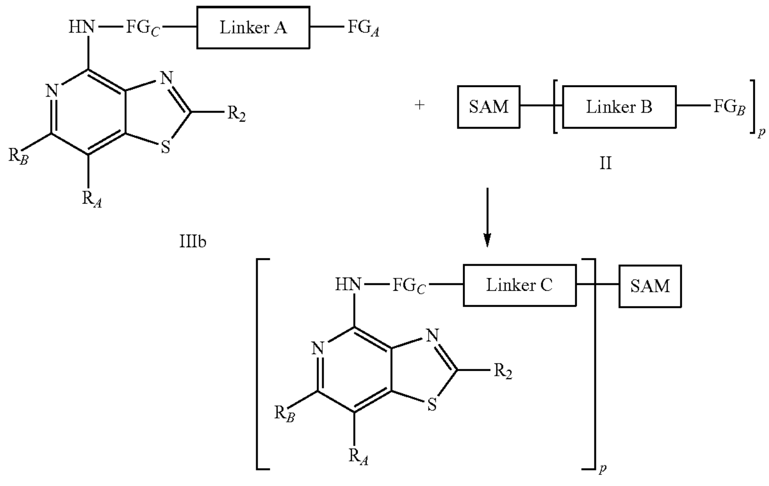

IIIb

II

Ib

For certain embodiments, the IRM conjugate is of the Formula Ib.

In some embodiments, conjugates of the invention can be prepared using the general method illustrated in Reaction Scheme IV, wherein SAM, $FG_A$, $FG_B$, $FG_C$, Linker A, Linker B, Linker C, $R_A$, $R_B$, $R_1$, $R_2$, and p are as defined above.

In Reaction Scheme IV, a functionalized IRM of Formula IIIc, which is a subgenus of Formula III, is reacted with a functionalized SAM of Formula II to provide an IRM conjugate of Formula Ic, which is a subgenus of Formula I. The reaction can be carried out as described for step (3) of Reaction Scheme I.

Functionalized IRMs of Formula IIIc can be prepared using the general methods described in step (2) of Reaction Scheme I and using the methods described in greater detail below.

Functionalized SAMs of Formula II can be prepared as described in step (1) of Reaction Scheme I.

For certain embodiments, the IRM conjugate is of the Formula Ic.

In the IRM conjugates of Formulas Ia, Ib, and Ic, the labile bond is the HN-$FG_c$ bond, for example, an HN—C(O) bond, an HN—C(O)O bond, or an HN—C(═NH) bond.

In some embodiments, functionalized IRMs can be prepared using the general method illustrated in Reaction Scheme V, wherein $FG_A$, Linker A, $R_A$, $R_B$, $R_1$, and $R_2$ are as defined above and AAG is an acid activating group selected from an N-(3-dimethylaminopropyl)-N'-ethylcarbodiimide (EDC) activated acid; N-hydroxysuccinimide (NHS), sulfo-N-hydroxysuccinimide (sNHS), 4-nitrophenyl, chloride, bromide, anhydride or mixed anhydride, pentafluorophenyl ester, and tetrafluorophenyl ester.

In Reaction Scheme V, an IRM of Formula IV is reacted with a heterobifunctional crosslinker of Formula V to provide a functionalized IRM of Formula IIId, which is a subgenus of Formulas III and IIIa. The reaction may be carried out by adding a solution of an IRM of Formula IV Reaction Scheme IV

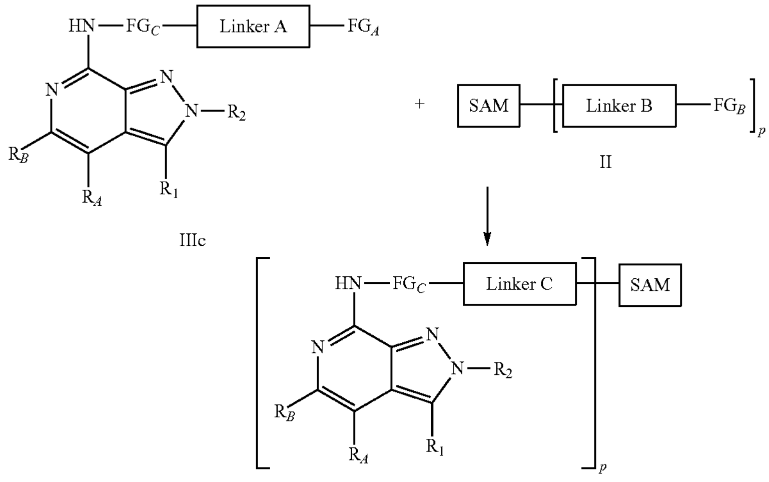

IIIc

II

Ic in a suitable solvent such as DMF to a solution of a crosslinker of Formula V in a suitable solvent such as DMF. The reaction may be carried out at ambient temperature or at a sub-ambient temperature such as, for example, 0° C.

Many IRMs of Formula IV are known; others can be prepared using known synthetic methods. See, for example, U.S. Pat. Nos. 4,689,338; 4,929,624; 5,266,575; 5,268,376; 5,346,905; 5,352,784; 5,389,640; 5,446,153; 5,756,747; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; 6,797,718; and 7,7091,214; and International Publication Nos. WO 2005/18551, WO 2005/18556, WO 2005/20999, WO 2005/032484, WO 2005/048933, WO 2005/048945, WO 2005/051317, WO 2005/051324, WO 2005/066169, WO 2005/066170, WO 2005/076783, WO 2005/094531, WO 2005/123079, WO 2005/123080, WO 2006/009832, WO 2006/028545, WO 2006/038923, WO 2006/065280, WO 2006/091394, WO 2006/086634, WO 2006/091567, WO 2006/091568, WO 2006/091647, and WO 2006/098852 and the references cited therein. Some heterobifunctional crosslinkers of Formula V are commercially available; others can be readily prepared using conventional synthetic methods.

Reaction Scheme V

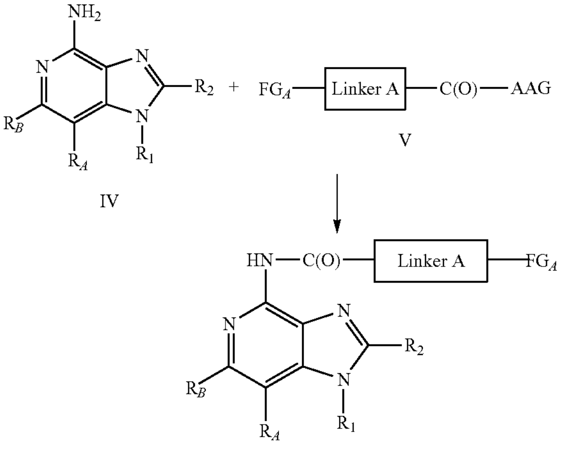

IV

V

IIId

In some embodiments, functionalized IRMs can be prepared using the general method illustrated in Reaction Scheme VI, wherein $FG_A$, Linker A, $R_A$, $R_B$, $R_1$, and $R_2$ are as defined above and G is selected from —Cl, —O—CH(C$_1$)CCl$_3$, —O-(4-nitrophenyl), NHS, and imidazole.

In Reaction Scheme VI, an IRM of Formula IV is reacted with a heterobifunctional crosslinker of Formula VI to provide a functionalized IRM of Formula IIIe, which is a subgenus of Formulas III and IIIa. The reaction may be carried out by adding a solution of an IRM of Formula IV in a suitable solvent such as DMF to a solution of a crosslinker of Formula VI in a suitable solvent such as DMF. The reaction may be carried out at ambient temperature or at a sub-ambient temperature such as, for example, 0° C.

As described in detail above, many IRMs of Formula IV are known; others can be prepared using known synthetic methods. Some heterobifunctional crosslinkers of Formula VI are commercially available; others can be readily prepared using conventional synthetic methods.

Reaction Scheme VI

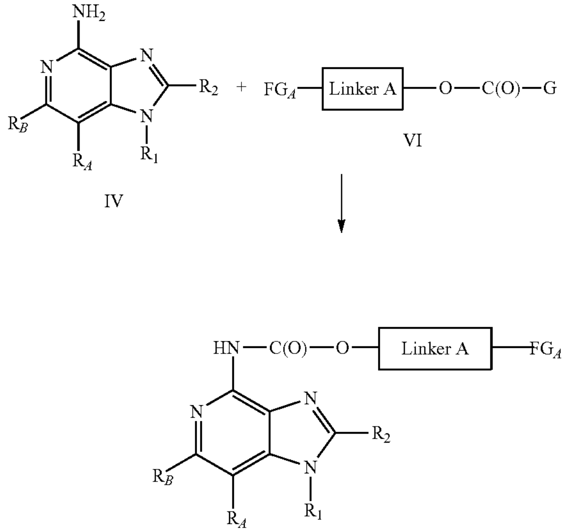

IV

VI

IIIe

In some embodiments, functionalized IRMs can be prepared using the general method illustrated in Reaction Scheme VII, wherein $FG_A$, Linker A, $R_A$, $R_B$, $R_1$, and $R_2$ are as defined above.

In Reaction Scheme VII, an IRM of Formula IV is reacted with a heterobifunctional crosslinker of Formula VII to provide a functionalized IRM of Formula IIIf, which is a subgenus of Formulas III and IIIa. The reaction may be carried out by adding a solution of an IRM of Formula IV in a suitable solvent such as DMF to a solution of a crosslinker of Formula VII in a suitable solvent such as DMF. The reaction may be carried out at ambient temperature or at a sub-ambient temperature such as, for example, 0° C.

As described in detail above, many IRMs of Formula IV are known, others can be prepared using known synthetic methods. Some heterobifunctional crosslinkers of Formula VII are commercially available; others can be readily prepared using conventional synthetic methods.

Reaction Scheme VII

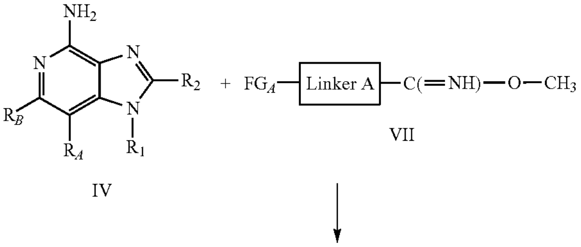

IV

VII

-continued

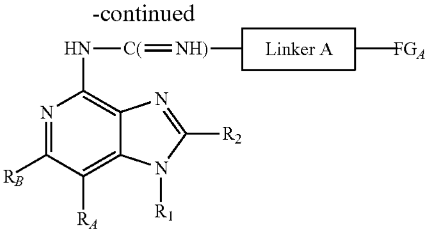

IIIf

In some embodiments, functionalized IRMs can be prepared using the general method illustrated in Reaction Scheme VIII, wherein $R_A$, $R_B$, $R_1$, and $R_2$ are as defined above, each R' is independently $C_{1-3}$ straight chain alkyl, $X_1$ is $C_{2-10}$ straight chain alkylene which may optionally be interrupted with a phenylene, or the R' groups and $X_1$, together with the nitrogen atoms to which they are attached, join to form a piperazine ring.

In step (1) of Reaction Scheme VIII, an IRM of Formula IV is reacted with succinic anhydride to provide a 2,5-dioxopyrrolidin-1-yl substituted compound of Formula IX. The reaction can be carried out by combining an IRM of Formula IV and succinic anhydride in a suitable solvent or solvent mix such as, for example, acetonitrile/DMF; and then heating the resulting mixture in a microwave reactor at an elevated temperature, such as, for example, 170° C.

In step (2) of Reaction Scheme VIII, a 2,5-dioxopyrrolidin-1-yl substituted compound of Formula IX is reacted with a diamine of Formula $H(R')N—X_1—N(R')H$ to provide an amido substituted compound of Formula X. The reaction can be carried out by combining a compound of Formula IX and the diamine in a suitable solvent such as, for example, ethyl acetate or acetonitrile; and then heating the resulting mixture in a microwave reactor at an elevated temperature, such as, for example, 110° C.

In step (3) of Reaction Scheme VIII, an amido substituted compound of Formula X is reacted with a maleimido substituted carboxylic acid of Formula XI to provide a functionalized IRM of Formula IIIg, which is a subgenus of Formulas III, IIIa, and IIId. The reaction can be carried out in two steps; (i) a solution of a carboxylic acid of Formula XI in a suitable solvent such as, for example, DMF, is treated sequentially with 1-hydroxybenzotriazole and N-(3-dimethylaminopropyl)-N'-ethylcarbodiimide hydrochloride to activate the acid; and (ii) a solution of a compound of Formula X in a suitable solvent such as, for example, DMF, is added in a controlled fashion to the solution of activated acid. Both steps can be carried out at ambient temperature. The functionalized IRM of Formula IIIg can be isolated using conventional methods.

As described in detail above, many IRMs of Formula IV are known, others can be prepared using known synthetic methods. Some maleimido substituted carboxylic acids of Formula XI are commercially available; others can be readily prepared using conventional synthetic methods.

Reaction Scheme VIII

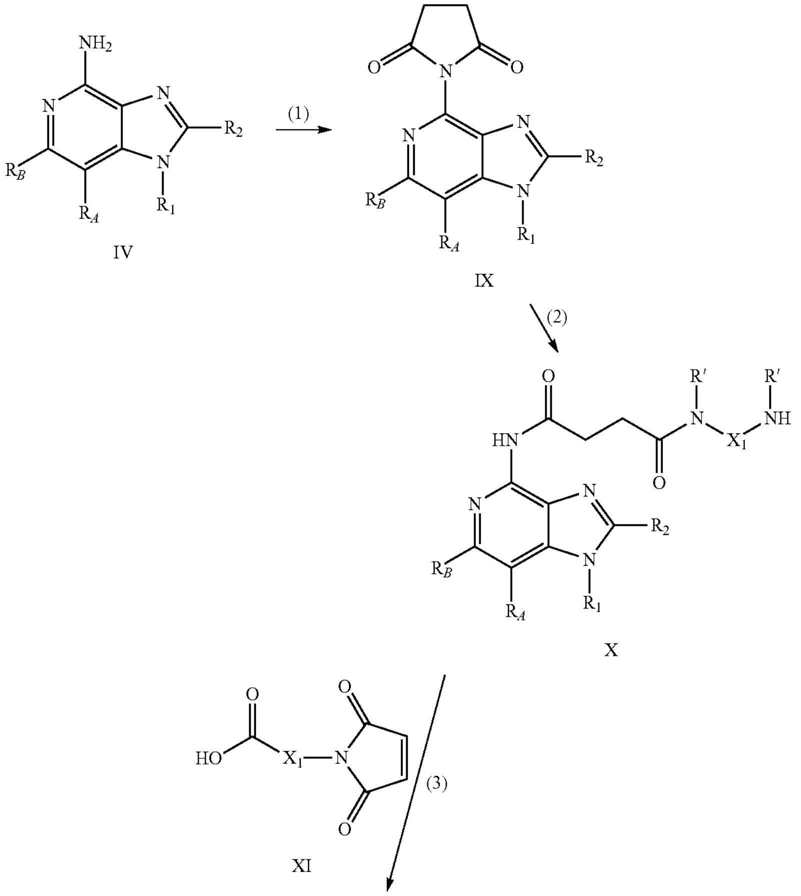

IV

IX

X

XI

-continued

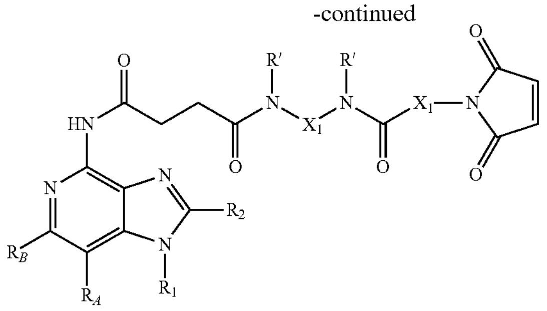

IIIg

In some embodiments, functionalized IRMs can be prepared according to the methods described in Reaction Schemes V, VI, VII, and VIII using IRMs of Formula XII or XIII, wherein $R_A$, $R_B$, $R_1$, and $R_2$ are as defined above, in lieu of an IRM of Formula IV.

XII

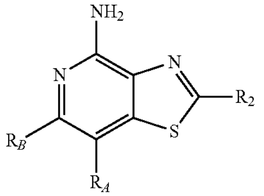

XIII

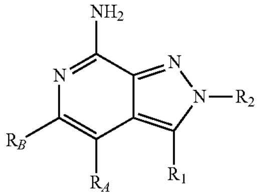

Many IRMs of Formulas XII and XIII are known; others can be prepared using known synthetic methods. See, for example, U.S. Pat. No. 6,110,929 and International Publication Nos. WO 2005/079195, WO 2006/107753, WO 2006/093514, WO 2006/009826, and WO 2006/086449.

In some embodiments, functionalized IRMs can be prepared using the general method illustrated in Reaction Scheme IX, wherein $FG_A$, Linker A, $R_A$, $R_B$, $R_1$, and AAG are as defined above and $X_2$ is $C_{1-4}$ straight chain alkylene.

In Reaction Scheme IX, an IRM of Formula XIV is reacted with a heterobifunctional crosslinker of Formula V to provide a functionalized IRM of Formula IIIh, which is a subgenus of Formula III. The reaction may be carried out by adding a solution of an IRM of Formula XIV in a suitable solvent such as DMF to a solution of crosslinker of Formula V in a suitable solvent such as DMF. Preferably, only about one equivalent of the crosslinker of Formula V is used. The reaction may be carried out at ambient temperature or at a sub-ambient temperature such as, for example, 0° C.

Many IRMs of Formula XIV are known; others can be prepared using known synthetic methods. See, for example, U.S. Pat. No. 5,389,640 and International Publication Nos. WO 2006/091568, WO 2006/098852, WO 2006/091567, and WO 2006/091647. Some heterobifunctional crosslinkers of Formula V are commercially available; others can be readily prepared using conventional synthetic methods.

Reaction Scheme IX

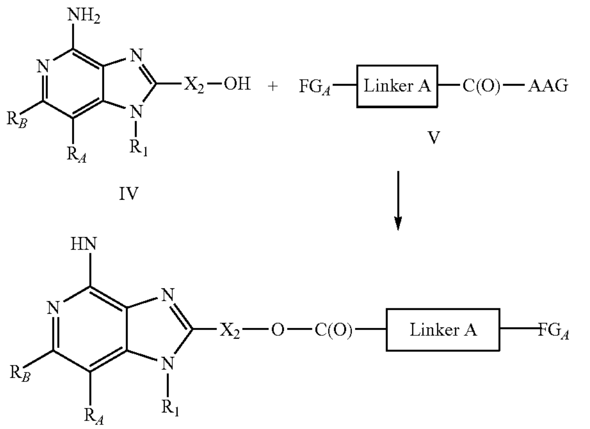

IV

V

IIIh

In some embodiments, the functional group on a heterobifunctional crosslinker used to form the labile bond on a functionalized IRM of Formula III may not be compatible with certain functional groups in the IRM. For example, in Reaction Scheme V the $R_1$ or $R_2$ group on an IRM of Formula IV may contain an amino or hydroxyl group. The amino or hydroxyl group may react with the heterobifunctional crosslinker of Formula V. In these cases it may be necessary to use a protecting group to temporarily mask the reactivity of the amino or hydroxyl group. The protecting group may then be removed at the appropriate step in the synthetic route. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

In one aspect, the present invention provides a functionalized IRM of Formula III, described above.

For certain embodiments, the functionalized IRM is of the Formula IIIa, IIIb, or IIIc. For certain of these embodiments, the functionalized IRM is of the Formula IIIa. For certain of these embodiments, the functionalized IRM is of the Formula IIId, IIIe, or IIIf. For certain of these embodiments, the functionalized IRM is of the Formula IIId. For certain of these embodiments, the functionalized IRM is of the Formula IIIg.

Unless otherwise specified, as used herein, the terms "alkyl," "alkenyl," "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. The terms, "alkylenyl", "alkenylenyl", and "alkynylenyl" are used when "alkylene", "alkenylene", and "alkynylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicylic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene", and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula $—N(R_8)—C(O)—N(R_8)—$ each $R_8$ group is independently selected. In another example, when two $R_{10}$ groups are present each $R_{10}$ group is independently selected.

The conjugate may be provided in any formulation suitable for administration to a subject. Suitable types of formulations are described, for example, in U.S. Pat. No. 5,238,944; U.S. Pat. No. 5,939,090; U.S. Pat. No. 6,245,776; European Patent No. EP 0 394 026; and U.S. Patent Publication No. 2003/0199538. The conjugate may be provided in any suitable form including but not limited to a solution, a suspension, an emulsion, or any form of mixture. The conjugate may be delivered in formulation with any pharmaceutically acceptable excipient, carrier, or vehicle. For example, the formulation may be delivered in a conventional topical dosage form such as, for example, a cream, an ointment, an aerosol formulation, a non-aerosol spray, a gel, a lotion, and the like. The formulation may further include one or more additives including but not limited to adjuvants, skin penetration enhancers, colorants, fragrances, flavorings, moisturizers, thickeners, and the like.

A formulation may be administered in any suitable manner such as, for example, non-parenterally or parenterally. As used herein, non-parenterally refers to administration through the digestive tract, including by oral ingestion. Parenterally refers to administration other than through the digestive tract such as, for example, intravenously, intramuscularly, transdermally, subcutaneously, transmucosally (e.g., by inhalation), or topically.

The composition of a formulation suitable for practicing the invention will vary according to factors known in the art including but not limited to the physical and chemical nature of the IRM moiety, the nature of the carrier, the intended dosing regimen, the state of the subject's immune system (e.g., suppressed, compromised, stimulated), the method of administering the IRM conjugate, and the species to which the formulation is being administered. Accordingly, it is not practical to set forth generally the composition of a formulation effective for all possible applications. Those of ordinary skill in the art, however, can readily determine an appropriate formulation with due consideration of such factors.

In some embodiments, the methods of the present invention include administering IRM conjugate to a subject in a formulation of, for example, from about 0.0001% to about 20% (unless otherwise indicated, all percentages provided herein are weight/weight with respect to the total formulation) to the subject, although in some embodiments the IRM conjugate may be administered using a formulation that provides IRM conjugate in a concentration outside of this range. In certain embodiments, the method includes administering to a subject a formulation that includes from about 0.01% to about 1% IRM conjugate, for example, a formulation that includes from about 0.1% to about 0.5% IRM conjugate.

An amount of an IRM conjugate effective for use in the methods of the present invention is an amount sufficient to provide an amount of free IRM compound after cleavage of the labile bond effective for generating an immune response. The precise amount of IRM conjugate will vary according to factors known in the art including but not limited to the physical and chemical nature of the IRM moiety, the nature of the carrier, the intended dosing regimen, the state of the subject's immune system (e.g., suppressed, compromised, stimulated), the method of administering the IRM conjugate, and the species to which the formulation is being administered. Accordingly, it is not practical to set forth generally the amount that constitutes an amount of IRM conjugate effective for use for all possible applications. Those of ordinary skill in the art, however, can readily determine the appropriate amount with due consideration of such factors.

In some embodiments, the methods of the present invention include administering sufficient IRM conjugate to provide a dose of, for example, from about 100 ng/kg to about 50 mg/kg to the subject, although in some embodiments the methods may be performed by administering IRM conjugate in a dose outside this range. In some of these embodiments, the method includes administering sufficient IRM conjugate to provide a dose of from about 10 μg/kg to about 5 mg/kg to the subject, for example, a dose of from about 100 μg/kg to about 1 mg/kg.

Alternatively, the dose may be calculated using actual body weight obtained just prior to the beginning of a treatment course. For the dosages calculated in this way, body surface area ($m^2$) is calculated prior to the beginning of the treatment course using the Dubois method: $m^2$=(wt $kg^{0.425}$×height $cm^{0.725}$)×0.007184.

In some embodiments, the methods of the present invention may include administering sufficient IRM conjugate to provide a dose of, for example, from about 0.01 mg/$m^2$ to about 10 mg/$m^2$.

The dosing regimen may depend at least in part on many factors known in the art including but not limited to the physical and chemical nature of the IRM moiety, the nature of the carrier, the amount of IRM conjugate being administered, the state of the subject's immune system (e.g., suppressed, compromised, stimulated), the method of administering the IRM conjugate, the half-life of the labile bond, and the species to which the formulation is being administered. Accordingly it is not practical to set forth generally the dosing regimen effective for use for all possible applications. Those of ordinary skill in the art, however, can readily determine an appropriate dosing regimen with due consideration of such factors.

In some embodiments of the invention, the IRM conjugate may be administered, for example, from a single dose to multiple doses per day. In certain embodiments, the IRM conjugate may be administered a single time. In other embodiments, the IRM conjugate may be administered on an "as needed" basis. In still other embodiments, the IRM conjugate may be administered from about once per year to about twice per day. For example, the IRM conjugate may be administered at least once per year, at least once every six months, at least once every four months, at least once every three months, at least once every two months, at least once every month, at least once every two weeks, at least once every week, at least twice per week, at least three times per week, at least five times per week, or at least once per day. Additionally, the IRM conjugate may be administered, for example, no more than once per day, no more than once per week, no more than once per month, or no more than once per year.

Conditions that may be treated by administering an IRM conjugate include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus*, or *Bordetella;*

(c) other infectious diseases, such *chlamydia*, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, an IRM conjugate may be useful as a vaccine adjuvant for use in conjunction with any material that raises either humoral and/or cell-mediated immune response, such as, for example, live viral, bacterial, or parasitic immunogens; inactivated viral, tumor-derived, protozoal, organism-derived, fungal, or bacterial immunogens, toxoids, toxins; self-antigens; polysaccharides; proteins; glycoproteins; peptides; cellular vaccines; DNA vaccines; autologous vaccines; recombinant proteins; glycoproteins; peptides; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Certain IRM conjugates may be particularly helpful in individuals having compromised immune function. For example, certain conjugates may be used for treating the opportunistic infections and tumors that occur after suppression of cell mediated immunity in, for example, transplant patients, cancer patients and HIV patients.

The methods of the present invention may be performed on any suitable subject. Suitable subjects include but are not limited to animals such as, for example, humans, non-human primates, poultry, fowl, rodents, dogs, cats, horses, pigs, sheep, goats, or cows.

EXAMPLES

The following examples have been selected merely to further illustrate features, advantages, and other details of the invention. It is to be expressly understood, however, that while the examples serve this purpose, the particular materials and amounts used as well as other conditions and details are not to be construed in a matter that would unduly limit the scope of this invention.

In the examples below automated flash chromatography was carried out using an INTELLIFLASH Flash Chromatography System (an automated flash purification system available from AnaLogix, Inc, Burlington, Wis., USA). The eluent used for each purification is given in the example. In some chromatographic separations, the solvent mixture 80/18/2 v/v/v chloroform/methanol/concentrated ammonium hydroxide (CMA) was used as the polar component of the eluent. In these separations, CMA was mixed with chloroform in the indicated ratio.

In the examples below, heating in a microwave was carried out using an EMRYS Optimizer automated microwave synthesizer.

Example 1

N[1]-{2-[[4-(2,5-dioxo-2,5-dihydro-1H-pyrrol-1-yl) butanoyl](methyl)amino]ethyl}-N[4]-(2-ethyl-1-{4-[(methylsulfonyl)amino]butyl}-1H-imidazo[4,5-c] quinolin-4-yl)-N[1]-methylsuccinamide

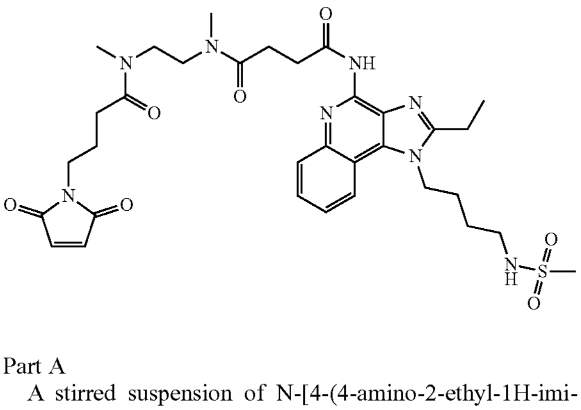

Part A

A stirred suspension of N-[4-(4-amino-2-ethyl-1H-imidazo[4,5-c]quinolin-1-yl)butyl]methanesulfonamide (2.00 g, 5.53 mmol, 1.0 eq, Example 236 in U.S. Pat. No. 6,677,349) and succinic anhydride (3.32 g, 6.0 eq) in a mixture of acetonitrile (11.9 mL) and DMF (2.1 mL) was heated in a microwave at 170° C. for 10 minutes. Analysis by liquid chromatography/mass spectroscopy (LCMS) indicated clean conversion to product. The reaction mixture was allowed to stand overnight. Upon scratching the sides of the vessel, a voluminous solid precipitated. This material was isolated by filtration then rinsed with acetonitrile (2×10 mL) to provide 2.03 g of N-{4-[4-(2,5-dioxopyrrolidin-1-yl)-2-ethyl-1H-imidazo[4,5-c]quinolin-1-yl] butyl}methanesulfonamide as a white solid.

Part B

A stirred suspension of N-{4-[4-(2,5-dioxopyrrolidin-1-yl)-2-ethyl-1H-imidazo[4,5-c]quinolin-1-yl] butyl}methanesulfonamide (317 mg, 0.71 mmol, 1.0 eq) and N,N'-dimethylethylenediamine (0.77 mL, 10.0 eq) in acetonitrile (3.3 mL) was heated in a microwave at 110° C. for 40 minutes. The reaction was repeated using 1.0 g of starting material, 2.4 mL of diamine, and 10.5 mL of acetonitrile. The two runs were combined and concentrated under reduced pressure. The residue was dissolved in chloroform (150 mL), washed with water (1×100 mL), dried over magnesium sulfate, and then concentrated under reduced pressure to provide 1.3 g of white foam. This material was purified by automated flash chromatography (silica gel, eluting with a gradient of 50-100% CMA in chloroform over 4 column volumes (CV) then with 100% CMA over 4 CV) to provide a colorless glass. The glass was dried under high vacuum to provide 0.66 g of N[1]-(2-ethyl-1-{4-[(methylsulfonyl)amino]butyl}-1H-imidazo[4,5-c]quinolin-4-yl)-N[4]-methyl-N[4]-[2-(methylamino)ethyl]succinamide.

Part C

1-Hydroxybenzotriazole (185 mg, 1.1 eq) and N-(3-dimethylaminopropyl)-N'-ethylcarbodiimide hydrochloride (262 mg, 1.1 eq) were added sequentially to a stirred solution of 4-malemidobutyric acid (250 mg, 1.1 eq) in DMF (5 mL) and the reaction mixture was stirred for 1 hour. A suspension of the material from Part B (0.66 g, 1.2 mmol, 1.0 eq) in DMF (7 mL) was added dropwise. The reaction mixture was stirred for 1 hour and then concentrated under reduced pressure to remove the bulk of the DMF. The residue was diluted with chloroform (150 mL), washed with water (1×75 mL), dried over magnesium sulfate, and then concentrated under reduced pressure to provide a clear, colorless oil. The oil was purified by automated flash chromatography (silica gel, eluting with a gradient of 0-50% CMA in chloroform over 6 CV then with 50% CMA in chloroform over 2 CV) to provide 0.80 g of a glass. The glass was concentrated from methanol and dried under high vacuum at 45° C. to provide 619 mg of a partial foam. This material was purified by automated flash chromatography (silica gel, eluting with a gradient of 0-50% CMA in chloroform over 7 CV then with 50% CMA in chloroform over 2 CV) to provide an oil. The oil was concentrated from methanol (20 mL) then dried under vacuum (0.10 Torr, 13 Pa) at 35° C. to provide 505 mg of N[1]-{2-[[4-(2,5-dioxo-2,5-dihydro-1H-pyrrol-1-yl)butanoyl](methyl)amino]ethyl}-N[4]-(2-ethyl-1-{4-[(methylsulfonyl)amino]butyl}-1H-imidazo[4,5-c]quinolin-4-yl)-N[1]-methylsuccinamide as an amorphous white solid. Anal. calcd for $C_{33}H_{44}N_8O_7S$: C, 56.88; H, 6.36; N, 16.08. Found: C, 56.59; H, 6.61; N, 15.93.

Example 2

N[1]-{2-[[4-(2,5-dioxo-2,5-dihydro-1H-pyrrol-1-yl)butanoyl](methyl)amino]ethyl}-N[4]-(2-(ethoxymethyl)-1-{2-methyl-2-[(methylsulfonyl)amino]propyl}-1H-imidazo[4,5-c]quinolin-4-yl)-M-methylsuccinamide

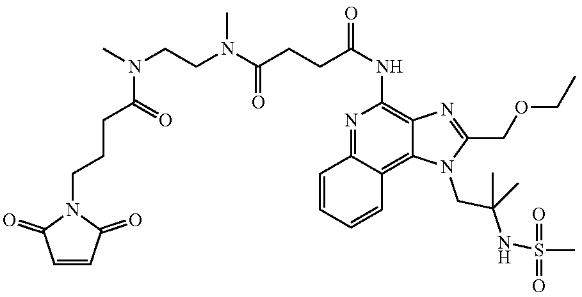 [SMILES: CCOCc1nc2c(NC(=O)CCC(=O)N(C)CCN(C)C(=O)CCCN3C(=O)C=CC3=O)nc3ccccc3c2n1CC(C)(C)NS(C)(=O)=O]

N[1]-{2-[[4-(2,5-dioxo-2,5-dihydro-1H-pyrrol-1-yl)butanoyl](methyl)amino]ethyl}-N[4]-(2-(ethoxymethyl)-1-{2-methyl-2-[(methylsulfonyl)amino]propyl}-1H-imidazo[4,5-c]quinolin-4-yl)-N[1]-methylsuccinamide was prepared according to the methods described in Example 1 using N-{2-[4-amino-2-(ethoxymethyl)-1H-imidazo[4,5-c]quinolin-1-yl]-1,1-dimethylethyl}methanesulfonamide (Example 268 in U.S. Pat. No. 6,677,349) in lieu of N-[4-(4-amino-2-ethyl-1H-imidazo[4,5-c]quinolin-1-yl)butyl]methanesulfonamide in Part A and with the further modification that the reaction in Part B was run at 100° C. using ethyl acetate as a solvent instead of acetonitrile. The product was provided as a white amorphous solid. Anal. calcd for $C_{34}H_{46}N_8O_8S.0.40H_2O$: C, 55.6; H, 6.42; N, 15.26. Found: C, 55.65; H, 6.49; N, 15.32.

Example 3

N[1]-{2-[[4-(2,5-dioxo-2,5-dihydro-1H-pyrrol-1-yl)butanoyl](methyl)amino]ethyl}-N[4]-(1-isobutyl-1H-imidazo[4,5-c]quinolin-4-yl)-N[1]-methylsuccinamide

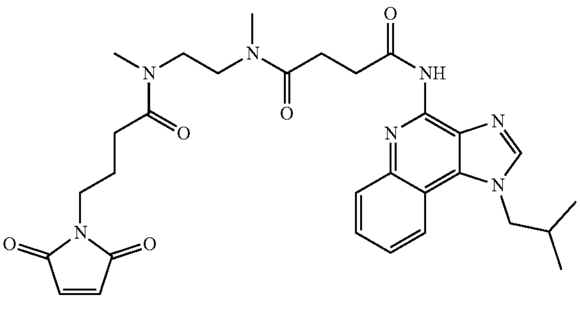 [SMILES: CC(C)Cn1cnc2c(NC(=O)CCC(=O)N(C)CCN(C)C(=O)CCCN3C(=O)C=CC3=O)nc3ccccc3c21]

Part A 1-(1-Isobutyl-1H-imidazo[4,5-c]quinolin-4-yl)pyrrolidine-2,5-dione was prepared according to the method described in Part A of Example 1 using 1-isobutyl-1H-imidazo[4,5-c]quinolin-4-amine (Example 99 in U.S. Pat. No. 4,689,338) in lieu of N-[4-(4-amino-2-ethyl-1H-imidazo[4,5-c]quinolin-1-yl)butyl]methanesulfonamide.

Part B

N,N'-dimethylethylenediamine (0.8 mL, 5.0 eq) was added to a stirred suspension of 1-(1-isobutyl-1H-imidazo[4,5-c]quinolin-4-yl)pyrrolidine-2,5-dione (500 mg, 1.5 mmol, 1.0 eq) in ethyl acetate (8 mL). The suspension was heated at 50° C. for 36 hours, cooled, and then concentrated under reduced pressure. The residue was diluted with chloroform (80 mL) and then washed with water (1×40 mL). The aqueous layer was back extracted with chloroform (1×40 mL). The combined organics were dried over magnesium sulfate and concentrated under reduced pressure to provide a white solid. The solid was suspended in chloroform and the suspension was filtered through a layer of CELITE filter aid to remove the insoluble material. The filtrate was purified by automated flash chromatography (silica gel, eluting with a gradient of 0-100% CMA in chloroform over 6 CV then with 100% CMA over 3 CV) to provide 0.40 g of N[1]-(1-isobutyl-1H-imidazo[4,5-c]quinolin-4-yl)-N[4]-methyl-N[4]-[2-(methylamino)ethyl]succinamide as an oil.

Part C

The material from Part B was reacted with activated 4-malemidobutyric acid using the method described in Part C of Example 1 except that the reaction was allowed to stir for 4 hours after the addition of the N[1]-(1-isobutyl-1H-imidazo[4,5-c]quinolin-4-yl)-N[4]-methyl-N[4]-[2-(methylamino)ethyl]succinamide. The crude product was purified by automated flash chromatography (silica gel, eluting with a gradient of 0-50% CMA in chloroform over 8 CV then with 50% CMA in chloroform over 2 CV) followed by drying under vacuum (0.12 Torr, 16 Pa) at 45° C. for 4 hours to provide 192 mg of N[1]-{2-[[4-(2,5-dioxo-2,5-dihydro-1H-pyrrol-1-yl)butanoyl](methyl)amino]ethyl}-N[4]-(1-isobutyl-1H-imidazo[4,5-c]quinolin-4-yl)-N[1]-methylsuccinamide as an amorphous white foam. Anal. calcd for $C_{30}H_{37}N_7O_5$: C, 62.59; H, 6.48; N, 17.03. Found: C, 62.25; H, 6.43; N, 17.02.

Example 4

N[1]-{2-[[4-(2,5-dioxo-2,5-dihydro-1H-pyrrol-1-yl)butanoyl](methyl)amino]ethyl}-N[1]-methyl-N[4]-(2-propyl[1,3]thiazolo[4,5-c]quinolin-4-yl)succinamide

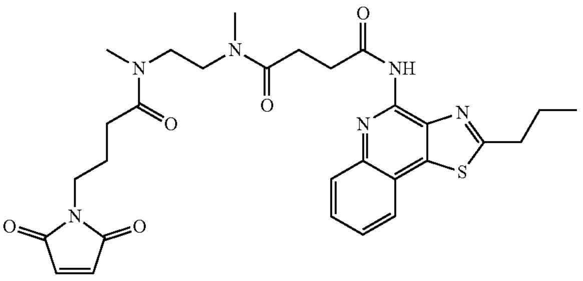 [SMILES: CCCc1nc2c(NC(=O)CCC(=O)N(C)CCN(C)C(=O)CCCN3C(=O)C=CC3=O)nc3ccccc3c2s1]

N[1]-{2-[[4-(2,5-dioxo-2,5-dihydro-1H-pyrrol-1-yl)butanoyl](methyl)amino]ethyl}-N[1]-methyl-N[4]-(2-propyl[1,3]thiazolo[4,5-c]quinolin-4-yl)succinamide was prepared according to the methods described in Example 3 using 2-propyl[1,3]thiazolo[4,5-c]quinolin-4-amine (Example 12 in U.S. Pat. No. 6,110,929) in lieu of 1-isobutyl-1H-imidazo[4,5-c]quinolin-4-amine in Part A and with the further modification that the reaction mixture in Part B was heated for 5 hours and the reaction mixture in Part C was allowed to stir overnight. The product was provided as a foam. Anal. calcd for $C_{29}H_{34}N_6O_5S$: C, 60.19; H, 5.92; N, 14.52. Found: C, 59.88; H, 6.01; N, 14.23.

Example 5

N[1]-{2-[[4-(2,5-dioxo-2,5-dihydro-1H-pyrrol-1-yl) butanoyl](methyl)amino]ethyl}-N[4]-[2-(ethoxymethyl)-1-(2-hydroxy-2-methylpropyl)-1H-imidazo[4,5-c]quinolin-4-yl]-N[1]-methylsuccinamide

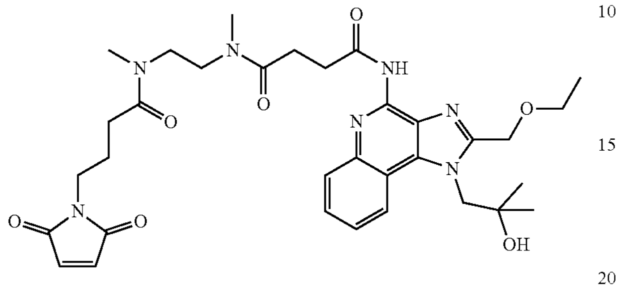

Part A

Succinic anhydride (10.0 g, 100 mmol) was added to a suspension of 4-amino-2-ethoxymethyl-α,α-dimethyl-1H-imidazo[4,5-c]quinoline-1-ethanol (31.4 g, 100 mmol, Example 99 in U.S. Pat. No. 5,389,640) in toluene (about 500 mL) and the reaction mixture was heated to reflux. Additional succinic anhydride (10.0 g) was added after 24 hours and again after 72 hours. The reaction was heated for a total of 6 days and then allowed to cool. A white solid was isolated by filtration. The solid was twice triturated with methanol, filtered, and dried. The resulting solid was suspended in methanol (300 mL). The suspension was heated at reflux for 2 hours and then allowed to cool. A solid was isolated by filtration and then dried under high vacuum at 100° C. to provide 29.6 g of 1-[2-(ethoxymethyl)-1-(2-hydroxy-2-methylpropyl)-1H-imidazo[4,5-c]quinolin-4-yl] pyrrolidine-2,5-dione.

Part B

Material from Part A (1 g, 2.5 mmol, 1 eq), N,N'-dimethylethylenediamine (1.35 mL, 5.0 eq), 4-(dimethylamino)pyridine (30 mg, 0.1 eq), and tetrahydrofuran (13 mL) were combined and heated at 50° C. for 2 hours. A small amount of chloroform and DMF were added and heating was continued for 1 day. The reaction mixture was allowed to stand at ambient temperature for 4 days. The reaction mixture was diluted with chloroform (150 mL) then washed with water (2×75 mL) and brine (1×75 mL). The organic layer was dried over magnesium sulfate and then concentrated under reduced pressure. The residue was purified by automated flash chromatography (silica gel, eluting with 50% CMA in chloroform for 1 CV, a gradient of 50-100% CMA in chloroform over 4 CV, and then with 100% CMA over 2 CV) to provide 0.49 g of N[1]-[2-(ethoxymethyl)-1-(2-hydroxy-2-methylpropyl)-1H-imidazo [4,5-c]quinolin-4-yl]-N[4]-methyl-N[4]-[2-(methylamino) ethyl]succinamide as a white foam.

Part C

The material from Part B was reacted with activated 4-malemidobutyric acid using the method described in Part C of Example 1 except that the reaction was allowed to stir for 2 hours after the addition of the N[1]-[2-(ethoxymethyl)-1-(2-hydroxy-2-methylpropyl)-1H-imidazo[4,5-c]quinolin-4-yl]-N[4]-methyl-N[4]-[2-(methylamino)ethyl]succinamide. The crude product was purified by automated flash chromatography (silica gel, eluting with a gradient of 0-50% CMA in chloroform over 8 CV then with 50% CMA in chloroform over 2 CV) followed by drying under vacuum (0.10 Torr, 13 Pa) with periodic careful warming with a heat gun to provide 480 mg of N[1]-{2-[[4-(2,5-dioxo-2,5-dihydro-1H-pyrrol-1-yl)butanoyl](methyl)amino]ethyl}-N[4]-[2-(ethoxymethyl)-1-(2-hydroxy-2-methylpropyl)-1H-imidazo[4,5-c]quinolin-4-yl]-N[1]-methylsuccinamide. Anal. calcd for $C_{33}H_{43}N_7O_7.1.18H_2O$: C, 59.07; H, 6.81; N, 14.61. Found: C, 58.71; H, 6.60; N, 14.38.

The compounds that were used as controls to the above exemplary compounds are shown in Table 1 below.

TABLE 1

| Compound | Chemical Name | Reference |
|---|---|---|
| Control 1 | N-[4-(4-amino-2-ethyl-1H-imidazo[4,5-c]quinolin-1-yl)butyl]methanesulfonamide | U.S. Pat. No. 6,677,349 Example 236 |
| Control 2 | N-{2-[4-amino-2-(ethoxymethyl)-1H-imidazo[4,5-c]quinolin-1-yl]-1,1-dimethylethyl}methanesulfonamide | U.S. Pat. No. 6,677,349 Example 268 |
| Control 3 | 1-(2-methylpropyl)-1H-imidazo[4,5-c]quinolin-4-amine | U.S. Pat. No. 4,689,338 Example 99 |
| Control 4 | 2-propylthiazolo[4,5-c]quinolin-4-amine | U.S. Pat. No. 6,110,929 Example 12 |
| Control 5 | 4-amino-α,α-dimethyl-2-ethoxymethyl-1H-imidazo[4,5-c]quinolin-1-ethanol | U.S. Pat. No. 5,389,640 Example 99 |

Example 6

Figure 2:
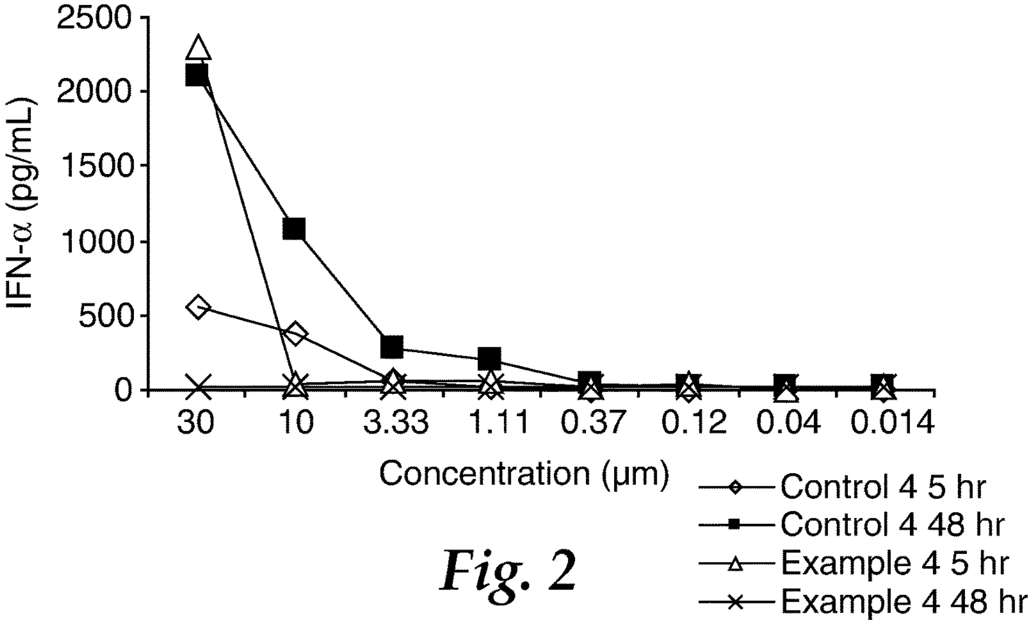
FIG. 2 is a line graph comparing IFN-α induction by an IRM conjugate composition of the invention compared to its parent IRM compound.
Figure 3:
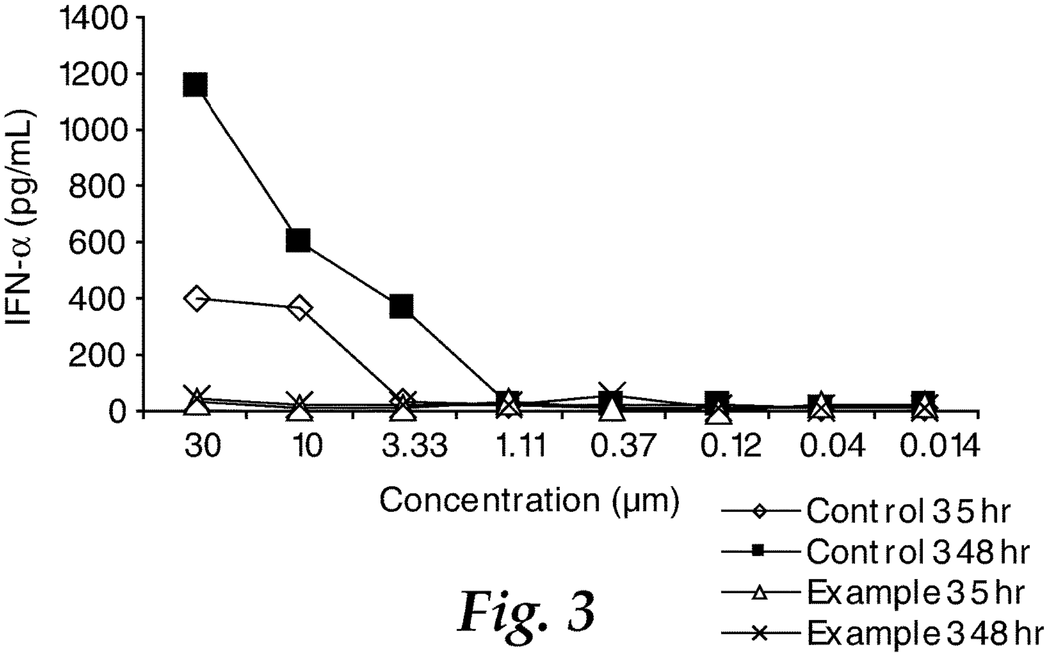
FIG. 3 is a line graph comparing IFN-α induction by an IRM conjugate composition of the invention compared to its parent IRM compound.
Figure 4:
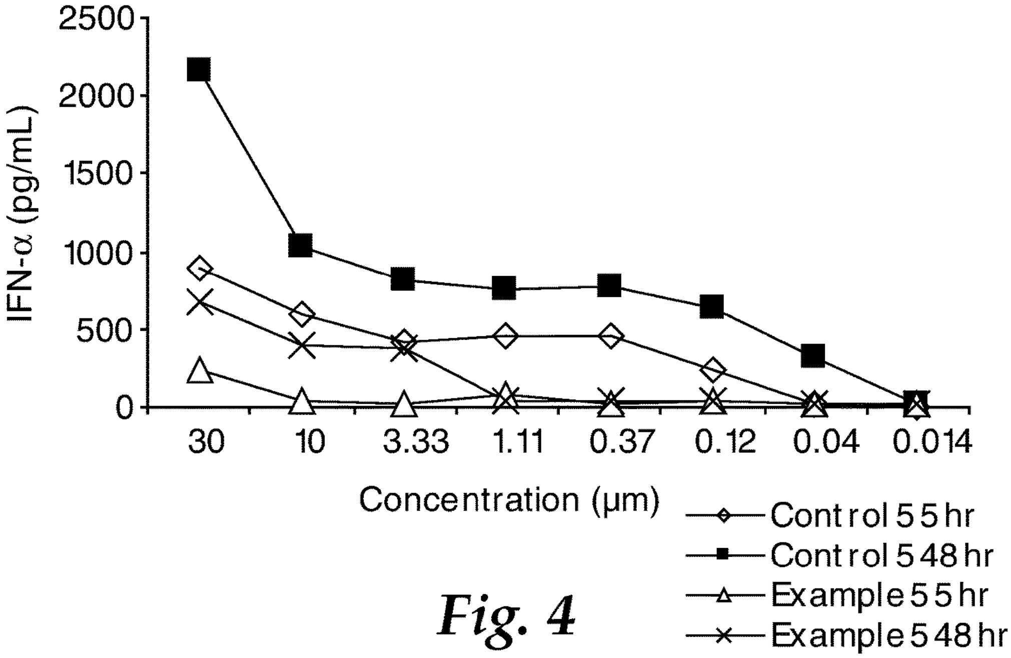
FIG. 4 is a line graph comparing IFN-α induction by an IRM conjugate composition of the invention compared to its parent IRM compound.
Figure 5:
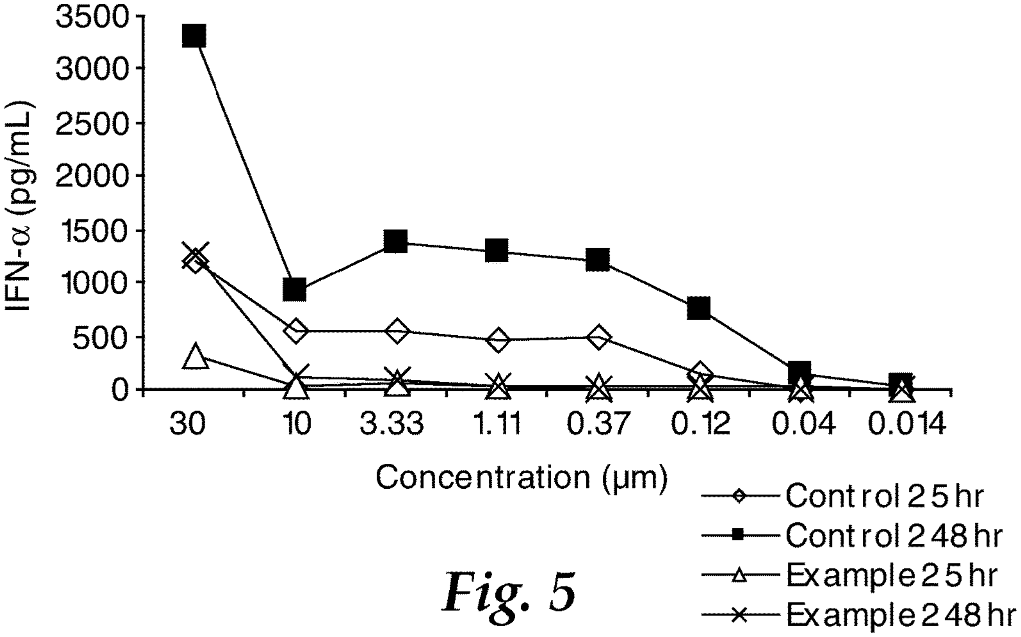
FIG. 5 is a line graph comparing IFN-α induction by an IRM conjugate composition of the invention compared to its parent IRM compound.
Figure 6:
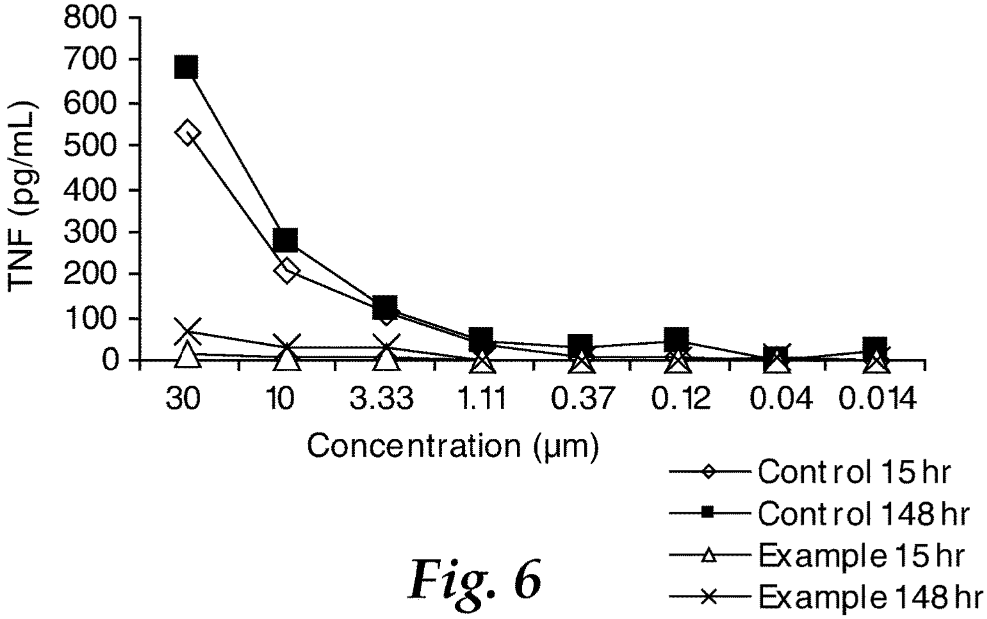
FIG. 6 is a line graph comparing TNF induction by an IRM conjugate composition of the invention compared to its parent IRM compound.
Figure 7:
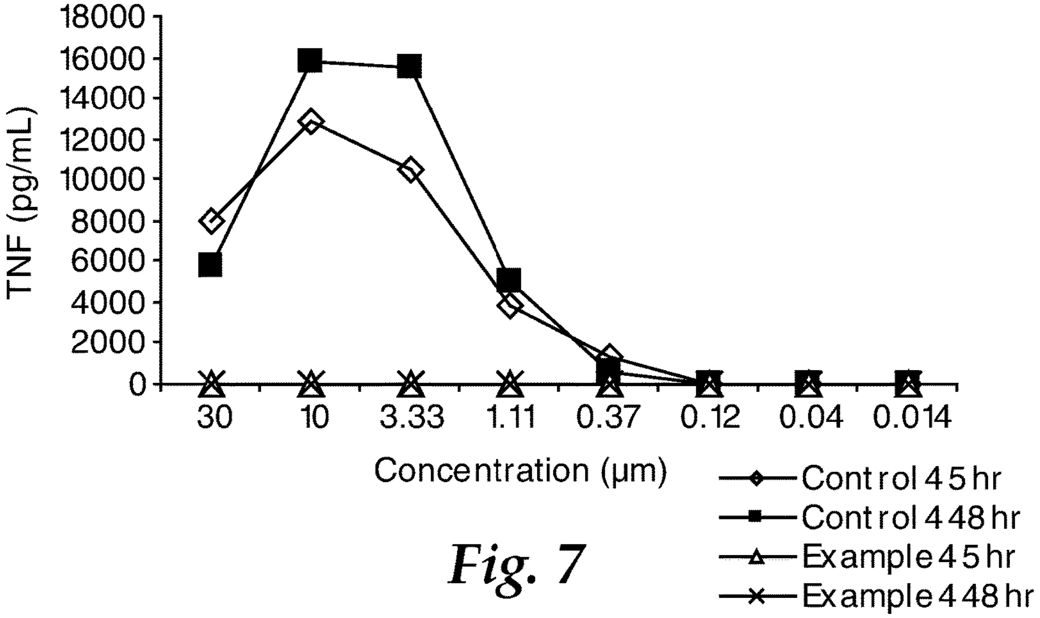
FIG. 7 is a line graph comparing TNF induction by an IRM conjugate composition of the invention compared to its parent IRM compound.
Figure 8:
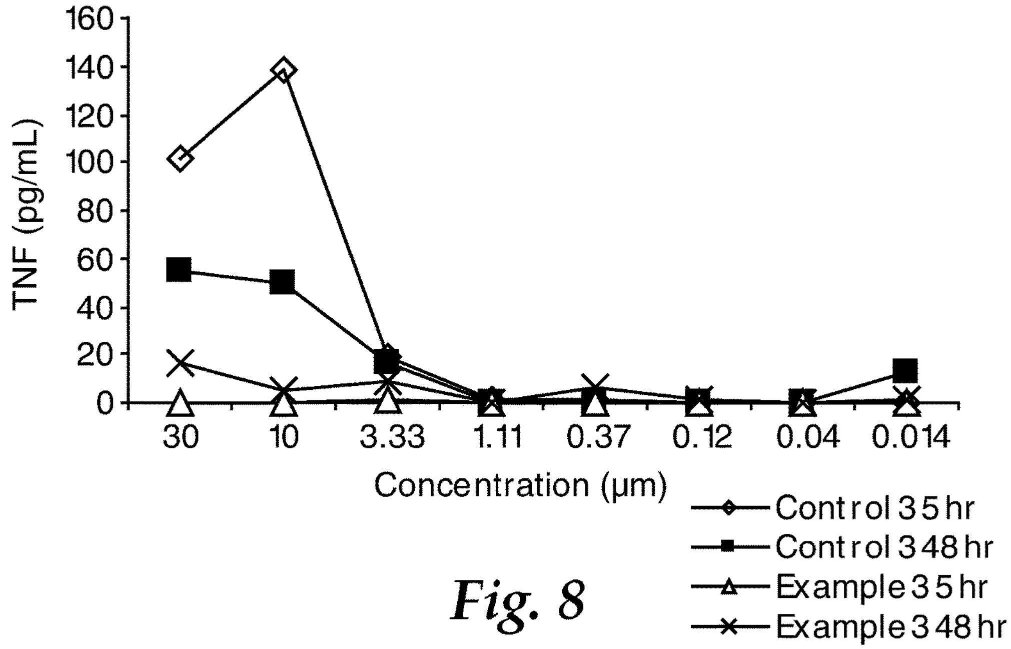
FIG. 8 is a line graph comparing TNF induction by an IRM conjugate composition of the invention compared to its parent IRM compound.
Figure 9:
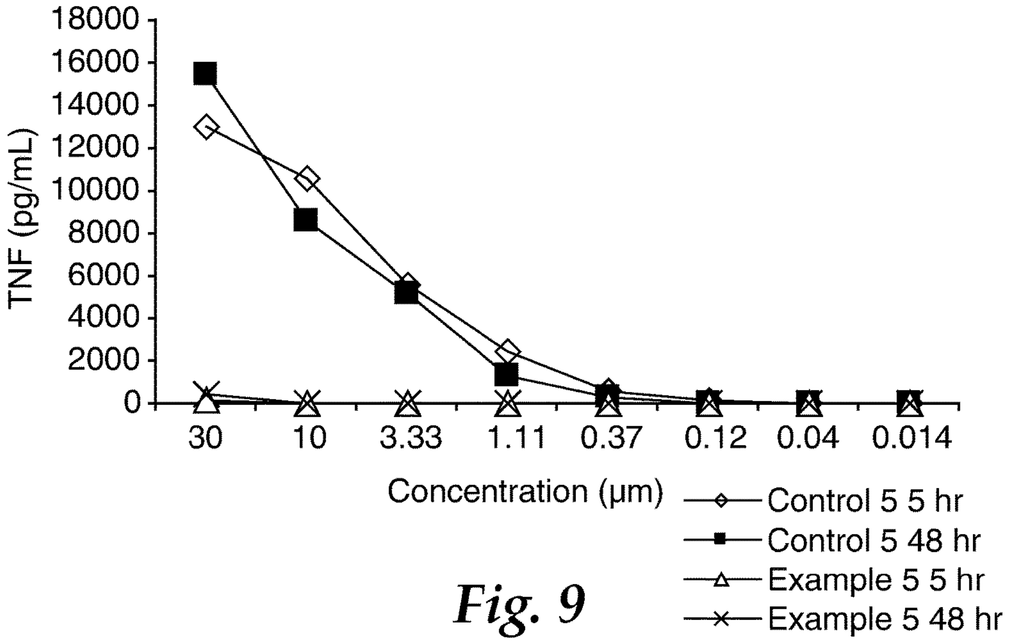
FIG. 9 is a line graph comparing TNF induction by an IRM conjugate composition of the invention compared to its parent IRM compound.
Figure 10:
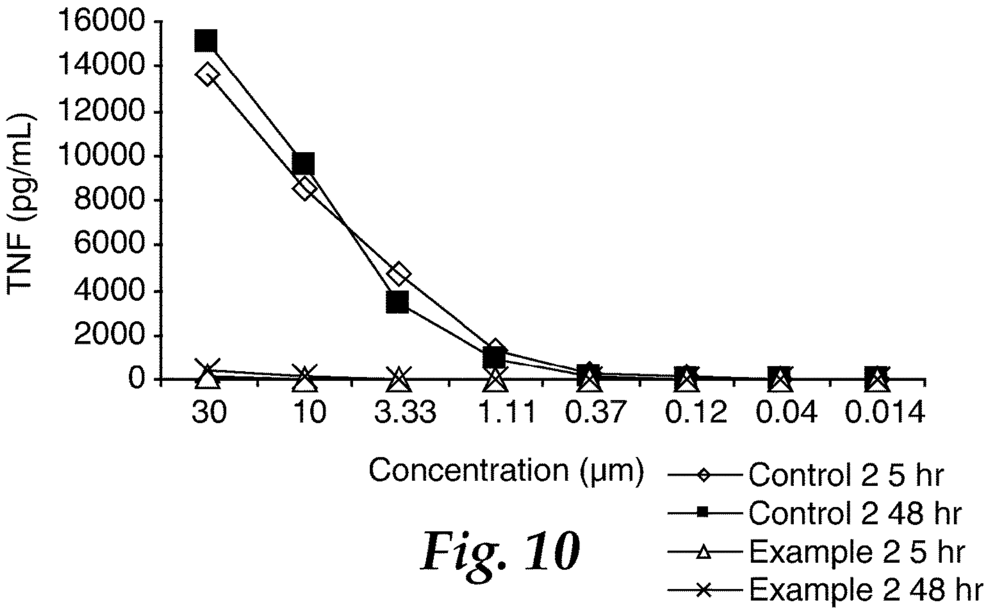
FIG. 10 is a line graph comparing TNF induction by an IRM conjugate composition of the invention compared to its parent IRM compound.

Whole blood from healthy human donors is collected by venipuncture into EDTA containing tubes. Peripheral blood mononuclear cells (PBMC) are separated from whole blood by density gradient centrifugation using HISTOPAQUE-1077 or Ficoll-Paque Plus. The PBMC layer is collected and washed twice with DPBS or HBSS and resuspended at $4\times10^6$ cells/mL in RPMI complete media. The PBMCs were added to a 96-well flat bottom sterile tissue culture plate (Corning Costar, Cambridge, Mass. or Becton Dickinson Labware, Lincoln Park, N.J.) to a final PBMC concentration of $2\times10^6$ cells/mL. The compounds were solubilized in dimethyl sulfoxide (DMSO) and tested at 3-fold serial dilution concentrations ranging from 30-0.014 μM. PBMCs were stimulated for five or 48 hours at 37° C. in a 5% carbon dioxide atmosphere. Following incubation the plates were centrifuged for 10 minutes at 1000 rpm (approximately 200×g) at 4° C. The cell-free culture supernatant were removed and transferred to sterile polypropylene tubes. Samples are maintained at −30 to −70° C. until analysis. Culture supernatants were analyzed for IFN-α and TNF production using a human IFN-α ELISA (PBL Biomedical Laboratories, Piscataway, N.J.) and human-specific TNF BV™ immunoassay (BioVeris Corp., Gaithersburg, Md.), respectively, with results expressed in pg/mL. IFN-α induction by the above control and exemplary compounds are shown in FIGS. 1-5. TNF induction by the above control and exemplary compounds are shown in FIGS. 6-10.

The complete disclosures of the patents, patent documents and publications cited herein are incorporated by reference in their entirety as if each were individually incorporated. In case of conflict, the present specification, including definitions, shall control.

Various modifications and alterations to this invention will become apparent to those skilled in the art without departing from the scope and spirit of this invention. Illustrative embodiments and examples are provided as examples only and are not intended to limit the scope of the present invention. The scope of the invention is limited only by the claims set forth as follows.

What is claimed is:

1. A method of generating an immune response comprising:

Administering, to a cell population capable of generating an IRM-induced immune response, an IRM conjugate of the formula Ia

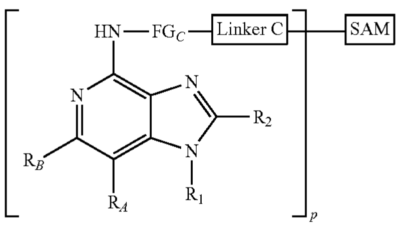

wherein:

when taken together, $R_A$ and $R_B$ form a fused aryl ring wherein the aryl ring is unsubstituted;

$R_1$ is selected from the group consisting of:

—$R_4$,
—X—$R_4$,
—X—Y—$R_4$,
—X—Y—X—Y—$R_4$, and
—X—$R_5$;

$R_2$ is selected from the group consisting of:

—$R_4$,
—X—$R_4$,
—X—Y—$R_4$, and
—X—$R_5$:

$R_3$ is selected from the group consisting of:

—Z—$R_4$,
—Z—X—$R_4$,
—Z—X—Y—$R_4$,
—Z—X—Y—X—Y—$R_4$, and
—Z—X—$R_5$;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:

—O—,
—$S(O)_{0-2}$—,
—$S(O)_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N($OR_9$)—,
—O—N($R_8$)-Q-,
—O—N═C($R_4$)—,
—C(═N—O—$R_8$)—,
—CH(—N(—O—$R_8$)-Q-$R_4$)—,

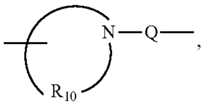, 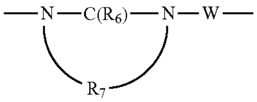,

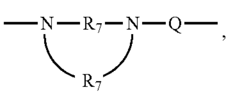, 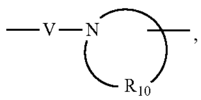, and

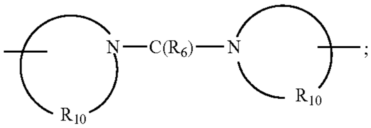;

Z is a bond or —O—;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of

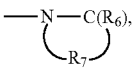, 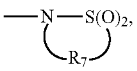, 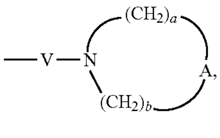,

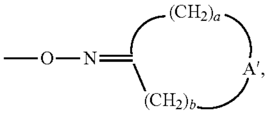, and

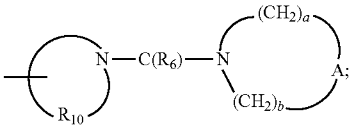;

$R_6$ is selected from the group consisting of ═O and ═S;

$R_7$ is $C_{2-7}$ alkylene;

$R_8$ is selected from the group consisting of hydrogen, alkyl, alkoxyalkylenyl, hydroxyalkylenyl, arylalkylenyl, and heteroarylalkylenyl;

$R_9$ is selected from the group consisting of hydrogen and alkyl;

$R_{10}$ is $C_{3-8}$ alkylene;

A is selected from the group consisting of —O—, —C(O)—, —$S(O)_{0-2}$—, and —N($R_4$)—;

A' is selected from the group consisting of —O—, —$S(O)_{0-2}$—, —N(-Q-$R_4$)—, and —$CH_2$—; Q is selected from the group consisting of a bond, —C($R_6$)—, —C($R_6$)—C($R_6$)—, —$S(O)_2$—, —C($R_6$)—N($R_8$)—W—, —$S(O)_2$—N($R_8$)—, —C($R_6$)—O—, —C($R_6$)—S—, and —C($R_6$)—N($OR_9$)—;

V is selected from the group consisting of —$C(R_6)$—, —O—$C(R_6)$—, —$N(R_8)$—$C(R_6)$—, and —$S(O)_2$—;

W is selected from the group consisting of a bond, —C(O)—, and —$S(O)_2$—;

a and b are independently integers from 1 to 6 with the proviso that a+b is ≤7;

SAM is a second active moiety wherein the SAM is other than a second IRM moiety;

$FG_C$ is selected from the group consisting of

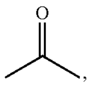, 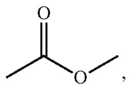, and 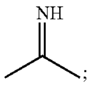;

Linker C is the reaction product of Linker A-$FG_A$ and Linker B-$FG_B$;

Linker A is $C_{1-10}$ alkylene, $C_{1-10}$ alkylene-arylene, arylene-$C_{1-10}$ alkylene, $C_3$-$C_8$ heterocyclene, $C_{1-10}$ alkylene-$C_{3-8}$ heterocyclene, or $C_{3-8}$ heterocyclene-$C_{1-10}$ alkylene;

Linker B is $C_{1-10}$ alkylene, O—$C_{1-8}$ alkylene-arylene, $C_{1-10}$ alkylene-arylene, arylene-$C_{1-10}$ alkylene, $C_3$-$C_8$ heterocyclene, $C_{1-10}$ alkylene-$C_{3-8}$ heterocyclene; or $C_{3-8}$ heterocyclene-$C_{1-10}$ alkylene;

p is an integer from 1 to 20; and $FG_A$ and $FG_B$ are capable of reacting with each other to form a covalent bond;

allowing a labile bond to be cleaved, thereby generating a free IRM compound; and allowing the free IRM compound to contact cells of the cell population, thereby generating an IRM-induced immune response.

2. The method of claim 1 wherein the cell population comprises dendritic cells, macrophages, cytotoxic T cells, NK cells, or NKT cells.

3. The method of claim 1 wherein the second active moiety comprises a targeting moiety.

4. The method of claim 3 wherein the targeting moiety comprises an active targeting moiety.

5. The method of claim 4 wherein the targeting moiety comprises an antibody, LHRH receptor ligand, or folic acid receptor ligand.

6. The method of claim 3 wherein the targeting moiety comprises a passive targeting moiety.

7. The method of claim 6 wherein the targeting moiety comprises a nanoparticle having a diameter of from about 50 nm to about 200 nm.

8. The method of claim 1 wherein $FG_C$ is

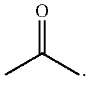.

9. The method of claim 1, wherein $FG_A$ is a nucleophilic group that is reactive to $FG_B$, and $FG_B$ is an electrophilic group.

10. The method of claim 1, wherein $FG_A$ is an electrophilic group that is reactive to $FG_B$, and $FG_B$ is a nucleophilic group.

11. The method of claim 1, wherein $FG_A$ is selected from the group consisting of —SH, 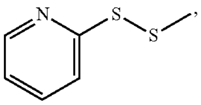, 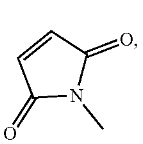,

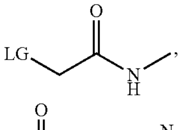, 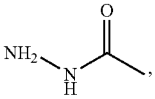, 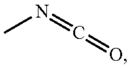,

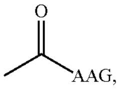, 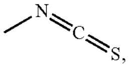, 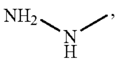,

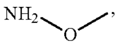, and 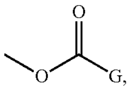, wherein LG is a leaving group selected from Cl, Br, I, O-mesyl or O-tosyl, and AAG is an acid activating group selected from N-(3-dimethylaminopropyl)-N'-ethylcarbodiimide activated acids, N-hydroxysuccinimide, sulfo-N-hydroxysuccinimide, 4-nitrophenyl, chloride, bromide, anhydride, mixed anhydride, pehtaflurophenyl ester, and tetraflurophenyl ester.

12. The method of claim 1, wherein $FG_B$ is selected from the group consisting of

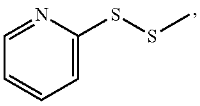, —SH, 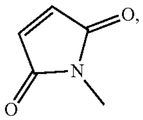

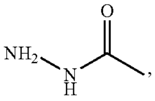, 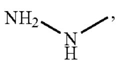, 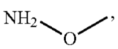,

—$NH_2$, and 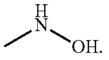.

13. The method of claim 1, wherein the IRM-induced immune response comprises production of cytokines.

* * * * *

UNITED STATES PATENT AND TRADEMARK OFFICE
CERTIFICATE OF CORRECTION

PATENT NO. : 10,144,735 B2
APPLICATION NO. : 16/016933
DATED : December 4, 2018
INVENTOR(S) : Doris Stoermer et al.

It is certified that error appears in the above-identified patent and that said Letters Patent is hereby corrected as shown below:

In the Specification

Column 5
Line 54, Delete "TLR 9." and insert -- TLR9. --, therefor.

Column 8
Line 26, Delete "hydroxyapetite" and insert -- hydroxyapatite --, therefor.
Line 36, Delete "Leuteinizing" and insert -- Luteinizing --, therefor.

Column 18
Line 57 (Approx.), After "(KMUH)" insert -- , --.

Column 19
Line 1, After "(PDPH)" insert -- , --.

Column 27
Line 55, Delete "(C1)" and insert -- (Cl) --, therefor.

Column 32 (Structure)

Lines 20-35, Delete " 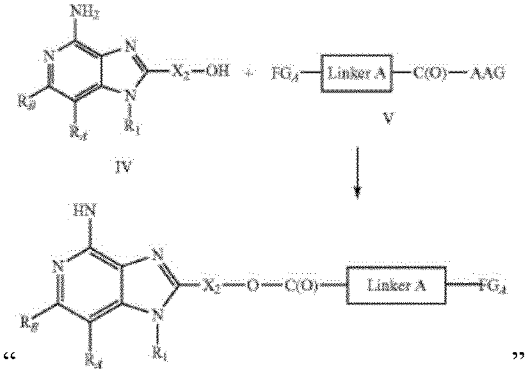 " and

Signed and Sealed this
Twenty-fifth Day of June, 2019

Andrei Iancu
*Director of the United States Patent and Trademark Office* insert -- 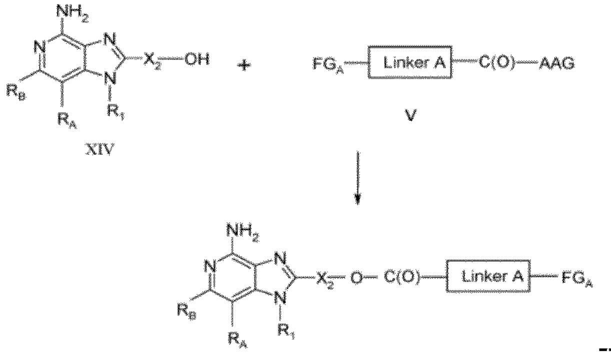 --, therefor.

<u>Column 33</u>
Line 64, Delete “bicylic” and insert -- bicyclic --, therefor.

<u>Column 36</u>
Line 67, Delete “hemophilus” and insert -- haemophilus --, therefor.

<u>Column 38</u>
Line 38, Delete “4-malemidobutyric” and insert -- 4-maleimidobutyric --, therefor.

<u>Column 39</u>
Line 6 (Approx.), Delete “M-” and insert -- N1- --, therefor.

<u>Column 40</u>
Line 21, Delete “4-malemidobutyric” and insert -- 4-maleimidobutyric --, therefor.

<u>Column 41</u>
Line 60, Delete “4-malemidobutyric” and insert -- 4-maleimidobutyric --, therefor.

In the Claims

<u>Column 43</u>
Line 8 (Approx.), In Claim 1, delete “Administering,” and insert -- administering, --, therefor.
Line 39 (Approx.), In Claim 1, delete “—X—R5:” and insert -- —X—R5; --, therefor.

<u>Column 46</u>
Line 35, In Claim 11, delete “pehtaflurophenyl” and insert -- pentafluorophenyl --, therefor.